(12) United States Patent
Hauser et al.

(10) Patent No.: US 10,688,195 B2
(45) Date of Patent: Jun. 23, 2020

(54) POLYMYXIN B-COATED NANOPARTICLES

(71) Applicants: Northwestern University, Evanston, IL (US); Midwestern University, Downers Grove, IL (US)

(72) Inventors: Alan R. Hauser, Chicago, IL (US); Andrew Lee, Chicago, IL (US); Marc H. Scheetz, Riverside, IL (US); Nathaniel J. Rhodes, Downers Grove, IL (US)

(73) Assignees: NORTHWESTERN UNIVERSITY, Evanston, IL (US); MIDWESTERN UNIVERSITY, Downers Grove, IL (US)

( * ) Notice: Subject to any disclaimer, the term of this patent is extended or adjusted under 35 U.S.C. 154(b) by 0 days.

(21) Appl. No.: 16/083,357

(22) PCT Filed: Mar. 17, 2017

(86) PCT No.: PCT/US2017/023006
§ 371 (c)(1),
(2) Date: Sep. 7, 2018

(87) PCT Pub. No.: WO2017/161296
PCT Pub. Date: Sep. 21, 2017

(65) Prior Publication Data
US 2019/0099500 A1    Apr. 4, 2019

Related U.S. Application Data

(60) Provisional application No. 62/309,793, filed on Mar. 17, 2016.

(51) Int. Cl.
*A61K 47/69* (2017.01)
*A61K 47/20* (2006.01)
(Continued)

(52) U.S. Cl.
CPC ............ *A61K 47/6929* (2017.08); *A61K 9/14* (2013.01); *A61K 9/51* (2013.01); *A61K 47/10* (2013.01);
(Continued)

(58) Field of Classification Search
CPC ...... A61K 47/6929; A61K 47/10; A61K 9/51; A61K 47/6923; A61K 47/20; A61K 38/12;
(Continued)

(56) References Cited

U.S. PATENT DOCUMENTS

2009/0148863 A1* 6/2009 Xu .................. G01N 33/54346
435/7.1
2009/0181101 A1* 7/2009 Rademacher ...... A61K 41/0052
424/499

OTHER PUBLICATIONS

Abdelarouf, K. et al. Characterization of polymyxin B-induced nephrotoxicity: implications for dosing regimen design. Antimicrob Agents Chemother. Sep. 2012;56(9):4625-9.
(Continued)

*Primary Examiner* — Carlos A Azpuru
(74) *Attorney, Agent, or Firm* — Casimir Jones SC; David W. Staple

(57) ABSTRACT

Provided herein are antibiotic coated nanoparticles and methods of treating bacterial infection therewith. In particular embodiments, polymyxin B, vancomycin, and/or other antibiotics are linked to nanoparticles (e.g., gold or silica nanoparticles) and utilized for the treatment of bacterial infections.

9 Claims, 17 Drawing Sheets

(51) Int. Cl.
A61K 9/14 (2006.01)
A61K 9/51 (2006.01)
A61K 47/10 (2017.01)
A61P 31/04 (2006.01)
A61K 31/43 (2006.01)
A61K 38/12 (2006.01)
A61K 38/14 (2006.01)
B82Y 5/00 (2011.01)

(52) U.S. Cl.
CPC .......... *A61K 47/20* (2013.01); *A61K 47/6923* (2017.08); *A61K 31/43* (2013.01); *A61K 38/12* (2013.01); *A61K 38/14* (2013.01); *A61P 31/04* (2018.01); *B82Y 5/00* (2013.01)

(58) Field of Classification Search
CPC .......... A61K 31/43; A61K 31/04; A61K 9/14; B82Y 5/00
See application file for complete search history.

(56) References Cited

OTHER PUBLICATIONS

Alexis, F, et al. Factors affecting the clearance and biodistribution of polymeric nanoparticles. Mol Pharm. Jul.-Aug. 2008;5(4):505-15.
Anonymous. 1997. Guidance for Industry. M3 Nonclinical Safety Studies for the Conduct of Human Clinical Trials for Pharmaceuticals. U.S. Department of Health and Human Services. Food and Drug Administration. Center for Drug Evaluation and Research (CDER). Center for Biologics Evaluation and Research (CBER).
Azad, M.A.K., et al. Structure-activity relationships of polymyxin antibiotics. Biochem Pharmacol. Aug. 1, 2012;84(3):278-91.
Bagheri, M, et al. Immobilization reduces the activity of surface-bound cationic antimicrobial peptides with no influence upon the activity spectrum. Antimicrob Agents Chemother. Mar. 2009;53(3):1132-41.
Bergen, PJ, et al. Polymyxin combinations: pharmacokinetics and pharmacodynamics for rationale use. Pharmacotherapy. Jan. 2015;35(1):34-42.
Berger, TJ, et al. Electrically generated silver ions: quantitative effects on bacterial and mammalian cells. Antimicrob Agents Chemother. Feb. 1976;9(2):357-8.
Boucher, HW, et al. Bad bugs, no drugs: no ESKAPE! An update from the Infectious Diseases Society of America. Clin Infect Dis. Jan. 1, 2009;48(1):1-12.
Brown, AN, et al. Nanoparticles functionalized with ampicillin destroy multiple-antibiotic-resistant isolates of Pseudomonas aeruginosa and Enterobacter aerogenes and methicillin-resistant *Staphylococcus aureus*. Appl Environ Microbiol. Apr. 2012;78(8):2768-74.
Burygin, GL, et al. On the enhanced antibacterial activity of antibiotics mixed with gold nanoparticles. Nanoscale Res Lett. Apr. 21, 2009;4(8):794-801.
Cartin-Ceba, R, et al. Risk factors for development of acute kidney injury in critically ill patients: a systematic review and meta-analysis of observational studies. Crit Care Res Pract. 2012;2012:691013.
CDC. 2013. Antibiotic resistance threats in the United States, 2013. http://www.cdc.gov/drugresistance/threat-report-2013/. Accessed Sep. 18.
Chamundeeswari, M, et al. Preparation, characterization and evaluation of a biopolymeric gold nanocomposite with antimicrobial activity. Biotechnol Appl Biochem. Jan. 25, 2010;55(1):29-35.
Choi, HS, et al. Renal clearance of quantum dots. Nat Biotechnol. Oct. 2007;25(10):1165-70.
Cigana, C, et al. Efficacy of the novel antibiotic POL7001 in preclinical models of Pseudomonas aeruginosa pneumonia. Antimicrob Agents Chemother. Jul. 22, 2016;60(8):4991-5000.
D'Agostino, C, et al. Microbiologic clearance following transition from standard infusion piperacillin-tazobactam to extended-infusion for persistent Gram-negative bacteremia and possible endocarditis: A case report and review of the literature. J Infect Chemother. Oct. 2015;21(10):742-6.
Dijkmans, AC, et al. Colistin: Revival of an old polymyxin antibiotic. Ther Drug Monit. Aug. 2015;37(4):419-27.
Diseases NIoAaI. 2014. NIAID's Antibacterial Resistance Program: Current Status and Future Directions 2014. https://www.niaid.nih.gov/sites/default/files/arstrategicplan2014.pdf. Accessed Apr. 19, 2019.
Dreaden, EC, et al. Size matters: gold nanoparticles in targeted cancer drug delivery. Ther Deliv. Apr. 2012;3(4):457-78.
Eby, DM, et al. Synthesis of bioinorganic antimicrobial peptide nanoparticles with potential therapeutic properties. Biomacromolecules 2008; 9:2487-2494.
Evans, ME, et al. Polymyxin B sulfate and colistin: old antibiotics for emerging multiresistant gram-negative bacteria. Ann Pharmacother. Sep. 1999;33(9):960-7.
Falagas, ME, et al. Toxicity after prolonged (more than four weeks) administration of intravenous colistin. BMC Infect Dis. Jan. 10, 2005;5:1.
Feltman, H, et al. Prevalence of type III secretion genes in clinical and environmental isolates of Pseudomonas aeruginosa. Microbiology. Oct. 2001;147(Pt 10):2659-69.
Fuchs, TC, et al. Biomarkers for drug-induced renal damage and nephrotoxicity-an overview for applied toxicology. AAPS J. Dec. 2011;13(4):615-31.
Garonzik, SM, et al. Population pharmacokinetics of colistin methanesulfonate and formed colistin in critically ill patients from a multicenter study provide dosing suggestions for various categories of patients. Antimicrob Agents Chemother. Jul. 2011;55(7):3284-94.
Gu, H.W., et al. Presenting vancomycin on nanoparticles to enhance antimicrobial activities. Nano Lett 3:1261-1263.
Guo, Q, et al. Identification of a small molecule that simultaneously suppresses virulence and antibiotic resistance of Pseudomonas aeruginosa. Sci Rep. Jan. 11, 2016;6:19141.
Han, WK, et al. Kidney Injury Molecule-1 (KIM-1): a novel biomarker for human renal proximal tubule injury. Kidney Int. Jul. 2002;62(1):237-44.
He, J, et al. A validated ultra-performance liquid chromatography-tandem mass spectrometry method for the quantification of polymyxin B in mouse serum and epithelial lining fluid: application to pharmacokinetic studies. J Antimicrob Chemother. May 2013;68(5):1104-10.
Huang, JX, et al. Cell- and biomarker-based assays for predicting nephrotoxicity. Expert Opin Drug Metab Toxicol. Dec. 2014;10(12):1621-35.
Humanes, B, et al. Protective effects of cilastatin against vancomycin-induced nephrotoxicity. Biomed Res Int. 2015;2015:704382.
Jensen, SA, et al. Spherical nucleic acid nanoparticle conjugates as an RNAi-based therapy for glioblastoma. Sci Transl Med. Oct. 30, 2013;5(209):209ra152.
Jeong, ES, et al. Characterization of urinary metabolites as biomarkers of colistin-induced nephrotoxicity in rats by a liquid chromatography/mass spectrometry-based metabolomics approach. Toxicol Lett. Apr. 25, 2016;248:52-60.
Kalil, AC, et al. Management of adults with hospital-acquired and ventilator-associated pneumonia: 2016 clinical practice guidelines by the Infectious Diseases Society of America and the American Thoracic Society. Clin Infect Dis. Sep. 1, 2016;63(5):e61-e111.
Keirstead, ND, et al. Early prediction of polymyxin-induced nephrotoxicity with next-generation urinary kidney injury biomarkers. Toxicol Sci. Feb. 2014;137(2):278-91.
Kenyon, EM. 2012. Computational Toxicology. In Reisfeld B, Mayeno A (ed), : vol. I, Methods in Molecular Biology, vol. 929. Springer Science.
Khlebstov, N, et al. Biodistribution and toxicity of engineered gold nanoparticles: a review of in vitro and in vivo studies. Chem Soc Rev. Mar. 2011;40(3):1647-71.
Liu, L,et al. Self-assembled cationic peptide nanoparticles as an efficient antimicrobial agent. Nat Nanotechnol 4:457-463.

(56) References Cited

OTHER PUBLICATIONS

Loo, AS, et al. Pharmacodynamic target attainment for various ceftazidime dosing schemes in high-flux hemodialysis. Antimicrob Agents Chemother. Dec. 2013;57(12):5854-9.

Mammen, M, et al. Polyvalent interactions in biological systems: Implications for design and use of multivalent ligands and inhibitors. Angew Chem Int Ed Engl. Nov. 2, 1998;37(20):2754-2794.

Micek, S, et al. An institutional perspective on the impact of recent antibiotic exposure on length of stay and hospital costs for patients with gram-negative sepsis. BMC Infect Dis. Mar. 13, 2012;12:56.

Nascimento, A, Jr.,et al. Hydration, ionic valence and cross-linking propensities of cations determine the stability of lipopolysaccharide (LPS) membranes. Chem Commun (Camb). Jan. 7, 20142014;50(2):231-3.

Neely, MN, et al. Accurate detection of outliers and subpopulations with Pmetrics, a nonparametric and parametric pharmacometric modeling and simulation package for R. Ther Drug Monit 2013; 34:467-476.

O'Donnell, JN, et al. Pharmacokinetics of centhaquin citrate in a dog model. J Pharm Pharmacol. Jun. 2016;68(6):803-9.

O'Donnell, JN, et al. Pharmacokinetics of centhaquin citrate in a rat model. J Pharm Pharmacol. Jan. 2016;68(1):56-62.

Okimura, K, et al. Chemical conversion of natural polymyxin B and colistin to their N-terminal derivatives. Chem Pharm Bull (Tokyo). Dec. 2007;55(12):1724-30.

Park, S, et al. Antimicrobial activity and cellular toxicity of nanoparticle-polymyxin B conjugates. Nanotechnology. May 6, 2011;22(18):185101.

Patel, N, et al. Identification of optimal renal dosage adjustments for traditional and extended-infusion piperacillin-tazobactam dosing regimens in hospitalized patients. Antimicrob Agents Chemother. Jan. 2010;54(1):460-5.

Payne, DJ, et al. Drugs for bad bugs: confronting the challenges of antibacterial discovery. Nat Rev Drug Discov. Jan. 2007;6(1):29-40.

Rai, a, et al. Antibiotic mediated synthesis of gold nanoparticles with potent antimicrobial activity and their application in antimicrobial coatings. J Maer Chem. 2010; 20:6789-6798.

Rai, A, et al. One-step synthesis of high-density peptide-conjugated gold nanoparticles with antimicrobial efficacy in a systemic infection model. Biomaterials. Apr. 2016;85:99-110.

Rashid, R, et al. Focal targeting of the bacterial envelope by antimicrobial peptides. Front Cell Dev Biol. Jun. 7, 2016;4:55.

Reed, MD, et al. The pharmacokinetics of colistin in patients with cystic fibrosis. J Clin Pharmacol. Jun. 2001;41(6):645-54.

Rhodes, NJ, et al. An exploratory analysis of the ability of a cefepime trough concentration greater than 22 mg/L to predict neurotoxicity. J Infect Chemother. Feb. 2016;22(2):78-83.

Rhodes, NJ, et al. Defining Clinical Exposures of Cefepime for Gram-Negative Bloodstream Infections That Are Associated with Improved Survival. Antimicrob Agents Chemother. Dec. 14, 2015.

Rhodes, NJ, et al. Evaluation of vancomycin exposures associated with elevations in novel urinary biomarkers of acute kidney injury in vancomycin-treated rats. Antimicrob Agents Chemother. Sep. 23, 2016;60(10):5742-51.

Rhodes, NJ, et al. Impact of loading doses on the time to adequate predicted beta-lactam concentrations in prolonged and continuous infusion dosing schemes. Clin Infect Dis. Sep. 15, 2014;59(6):905-7.

Rhodes, NJ, et al. Optimal timing of oral fosfomycin administration for pre-prostate biopsy prophylaxis. J Antimicrob Chemother. Jul. 2015;70(7):2068-73.

Rigatto, MH, et al. Multicenter prospective cohort study of renal failure in patients treated with colistin versus polymyxin B. Antimicrob Agents Chemother. Mar. 25, 2016;60(4):2443-9.

Rocco, M, et al. Risk factors for acute kidney injury in critically ill patients receiving high intravenous doses of colistin methanesulfonate and/or other nephrotoxic antibiotics: a retrospective cohort study. Crit Care. Aug. 14, 2013;17(4):R174.

Roy-Burman, A, et al. Type III protein secretion is associated with death in lower respiratory and systemic Pseudomonas aeruginosa infections. J Infect Dis. Jun. 15, 2001;183(12):1767-74.

Ruden, S, et al. Synergistic interaction between silver nanoparticles and membrane-permeabilizing antimicrobial peptides. Antimicrob Agents Chemother. Aug. 2009;53(8):3538-40.

Sabbisetti, VS, et al. Blood kidney injury molecule-1 is a biomarker of acute and chronic kidney injury and predicts progression to ESRD in type I diabetes. J Am Soc Nephrol. Oct. 2014;25(10):2177-86.

Sandri, AM, et al. Pharmacokinetics of polymyxin B in patients on continuous venovenous haemodialysis. J Antimicrob Chemother. Mar. 2013;68(3):674-7.

Sandri, AM, Landersdorfer CB, Jacob J, Boniatti MM, Dalarosa MG, Falci DR, Behle TF, Bordinhao RC, Wang J, Forrest A, Nation RL, Li J, Zavascki AP. 2013. Population pharmacokinetics of intravenous polymyxin B in critically ill patients: implications for selection of dosage regimens. Clin Infect Dis 57:524-531.

Santamaria, C, et al. Nephrotoxicity associated with the use of intravenous colistin. Scand J Infect Dis. 2009;41(10):767-9.

Shaver, CM, et al. Relative contributions of Pseudomonas aeruginosa ExoU, ExoS, and ExoT to virulence in the lung. Infect Immun. Dec. 2004;72(12):6969-77.

Simpson, DA, et al. Genetic analysis of Pseudomonas aeruginosa adherence: distinct genetic loci control attachment to epithelial cells and mucins. Infect Immun. Sep. 1992;60(9):3771-9.

Sistare, Fd, et al. Towards consensus practices to qualify safety biomarkers for use in early drug development. Nat Biotechnol. May 2010;28(5):446-54.

Tam, VH, et al. Pharmacodynamics of polymyxin B against Pseudomonas aeruginosa. Antimicrob Agents Chemother. Sep. 2005;49(9):3624-30.

Tarchini, G. Nephrotoxicity associated with intravenous colistin. Clin Infect Dis. Dec. 1, 2009;49(11):1773.

Tatarinova, T, et al. Two general methods for population pharmacokinetic modeling: non-parametric adaptive grid and non-parametric Bayesian. J Pharmacokinet Pharmacodyn. Apr. 2013;40(2):189-99.

Torrice, M. 2013. Antibacterial Boom and Bust. Chem Engineer News 91:34-37.

Tumbarello, M, et al. Clinical outcomes of Pseudomonas aeruginosa pneumonia in intensive care unit patients. Intensive Care Med. Apr. 2013;39(4):682-92.

Vaidya, VS, et al. Kidney injury molecule-1 outperforms traditional biomarkers of kidney injury in preclinical biomarker qualification studies. Nat Biotechnol. May 2010;28(5):478-85.

Wang, H, et al. The efficacy of self-assembled cationic antimicrobial peptide nanoparticles against Cryptococcus neoformans for the treatment of meningitis. Biomaterials. Apr. 2010;31(10):2874-81.

Wang, Y, et al. Clarification on precision criteria to derive sample size when designing pediatric pharmacokinetic studies. J Clin Pharmacol. Oct. 2012;52(10):1601-6.

Weiner, LM, et al. Antimicrobial-resistant pathogens associated with healthcare-associated infections: Summary of data reported to the National Healthcare Safety Network at the Centers for Disease Control and Prevention, 2011-2014. Infect Control Hosp Epidemiol. Nov. 2016;37(11):1288-1301.

Weinstein, J, et al. Selective chemical modifications of polymyxin B. Bioorg Med Chem Lett. Dec. 1, 1998;8(23):3391-6.

Whited, L, et al. Pharmacokinetics of Cefepime in Patients with Cancer and Febrile Neutropenia in the Setting of Hematologic Malignancies or Hematopoeitic Cell Transplantation. Pharmacotherapy. Sep. 2016;36(9):1003-10.

Woods, DE, et al. Role of pili in adherence of Pseudomonas aeruginosa to mammalian buccal epithelial cells. Infect Immun. Sep. 1980;29(3):1146-51.

Yousef, JM, et al. Ascorbic acid protects against the nephrotoxicity and apoptosis caused by colistin and affects its pharmacokinetics. J Antimicrob Chemother. Feb. 2012;67(2):452-9.

Yu, Z, et al. Antibacterial mechanisms of polymyxin and bacterial resistance. Biomed Res Int. 2015;2015:679109.

Yun, B, et al. Cellular uptake and localization of polymyxins in renal tubular cells using rationally designed fluorescent probes. Antimicrob Agents Chemother. Dec. 2015;59(12):7489-96.

(56) References Cited

OTHER PUBLICATIONS

Zhao, G, et al. Multiple parameters for the comprehensive evaluation of the susceptibility of *Escherichia coli* to the silver ion. Biometals. Jan. 1998;11(1):27-32.

* cited by examiner

POLYMYXIN B-COATED NANOPARTICLES

CROSS REFERENCE TO RELATED APPLICATIONS

The present invention claims the priority benefit of U.S. Provisional Patent Application 62/309,793, filed Mar. 17, 2016, which is incorporated by reference in its entirety.

FIELD

Provided herein are antibiotic coated nanoparticles and methods of treating bacterial infection therewith. In particular embodiments, polymyxin B, vancomycin, and/or other antibiotics are linked to nanoparticles (e.g., gold or silica nanoparticles) and utilized for the treatment of bacterial infections.

BACKGROUND

The emergence of bacteria that are highly resistant to conventional antibiotics, is a crisis in healthcare and has left clinicians squeezed between two opposing forces. The number of new antibiotics in the pharmaceutical pipeline has greatly diminished. Meanwhile, antibiotic resistance among bacterial pathogens is increasing at an alarming rate. Gram-negative bacteria such as Pseudomonas aeruginosa, Acinetobacter baumannii, and Klebsiella pneumoniae are especially problematic and have been designated "ESKAPE" pathogens because of their propensity to develop resistance to conventional antibiotics. Strategies are needed to treat these infections and address this crisis. Unfortunately, library screening for new classes of antibiotics has reached the point of diminishing returns, with frequent re-identification of already known drug classes. Approaches are required to provide new applications, and prolong the useful lifespan of conventional antibiotics.

SUMMARY

In some embodiments, provided herein are compositions comprising nanoparticles with surface-attached antibiotics displayed thereon. In some embodiments, the nanoparticles comprise a gold (Au) or silica core. In some embodiments, the antibiotics comprise polymyxin B and/or vancomycin. In some embodiments, the antibiotics further comprise additional peptidoglycan-binding antibiotics. In some embodiments, the additional peptidoglycan-binding antibiotics are beta-lactams. In some embodiments, the antibiotics are tethered to the surface of the nanoparticles by a linker. In some embodiments, the linker comprises PEG. In some embodiments, the linker comprises an alkyl chain. In some embodiments, the linker comprises $SH-(CH_2)_{4-30}(EG)_{2-12}OH$. In some embodiments, the linker comprises $SH-C_{11}H_{22}-EG_6OH$.

In some embodiments, provided herein are pharmaceutical preparations comprising the nanoparticle compositions herein.

In some embodiments, provided herein are methods of treating a bacterial infection in a subject comprising administering a pharmaceutical preparation described herein to the subject. In some embodiments, the pharmaceutical preparation is administered systemically. In some embodiments, the pharmaceutical preparation is administered locally to the site of the infection.

DEFINITIONS

Figure 1:
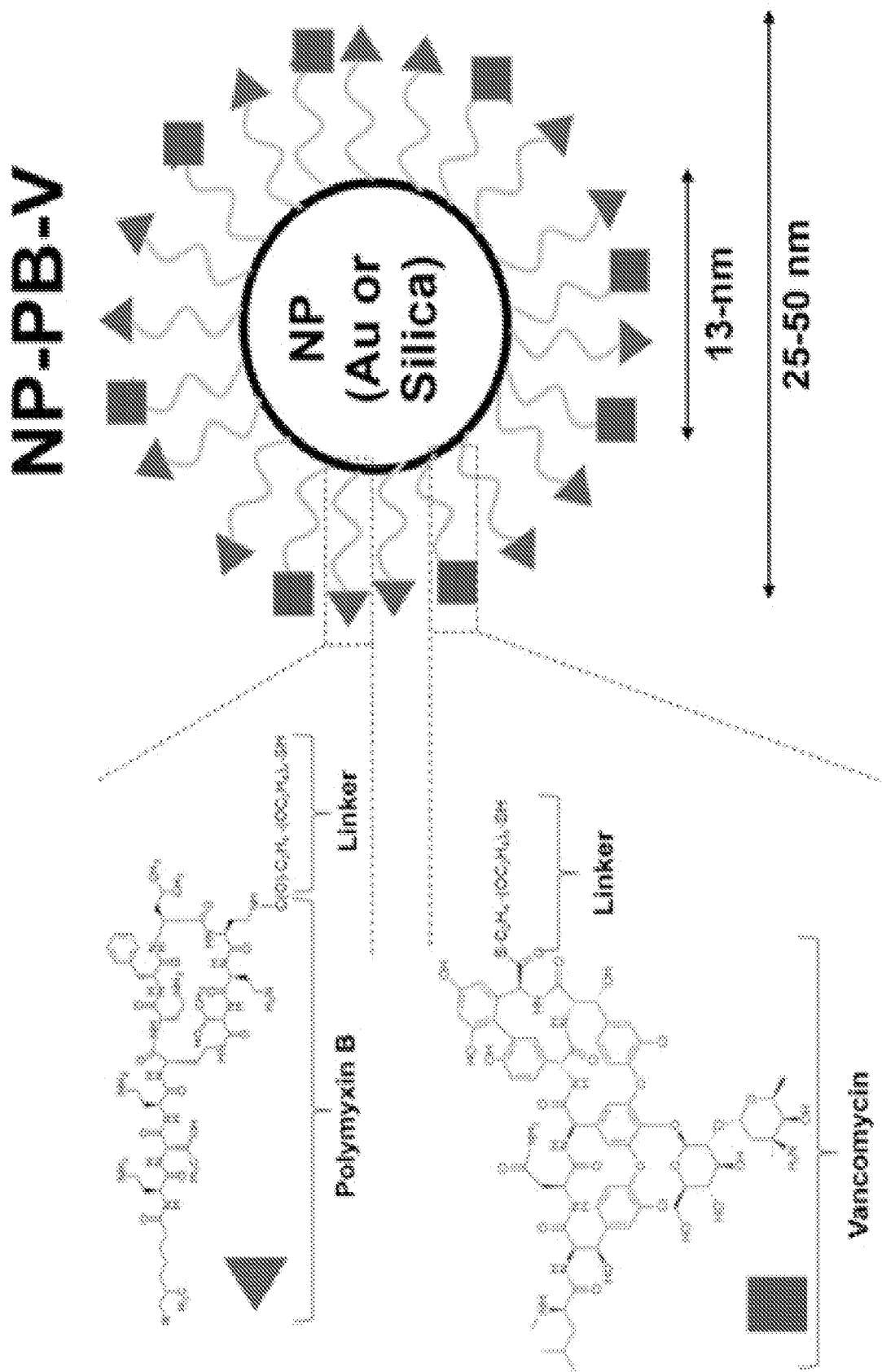
FIG. 1. Schematic of nanoparticles functionalized with polymyxin B and vancomycin. Linkers for conjugation of the antibiotics to Au nanoparticles are exemplified.
Figure 2:
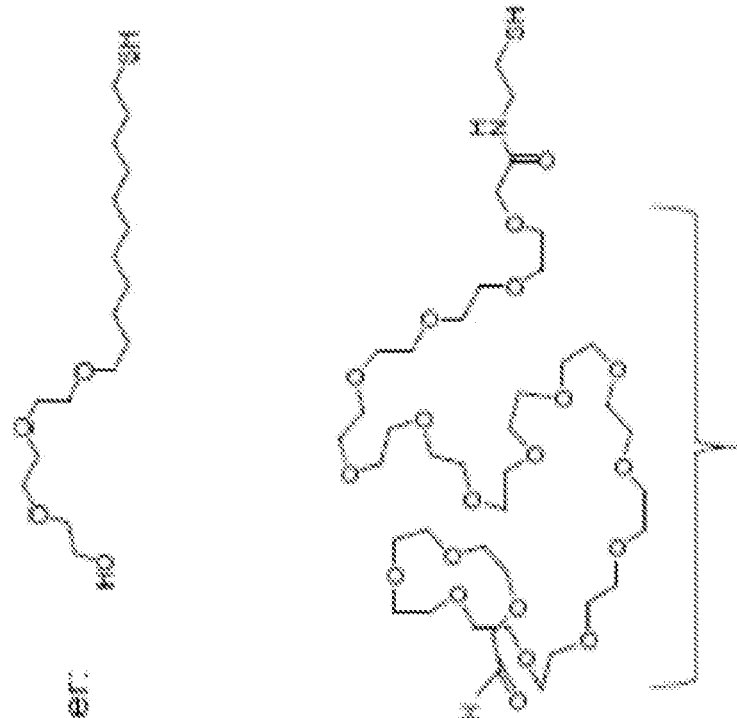
FIG. 2. Schematic of exemplary antibiotic/linker pendant.
Figure 3:
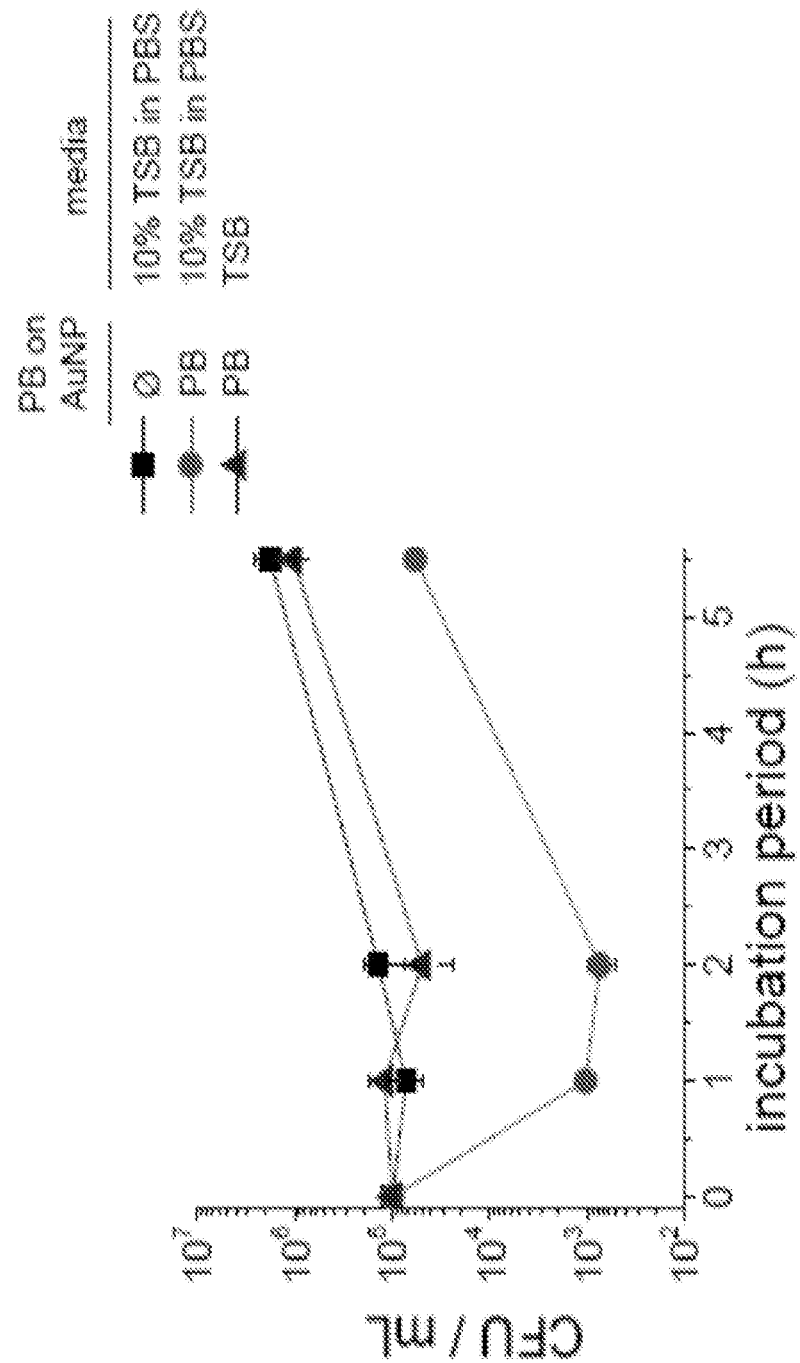
FIG. 3. Treatment of A. Baumannii with Au nanoparticles displaying the antibiotic/linker pendant depicted in FIG. 2.
Figure 4:
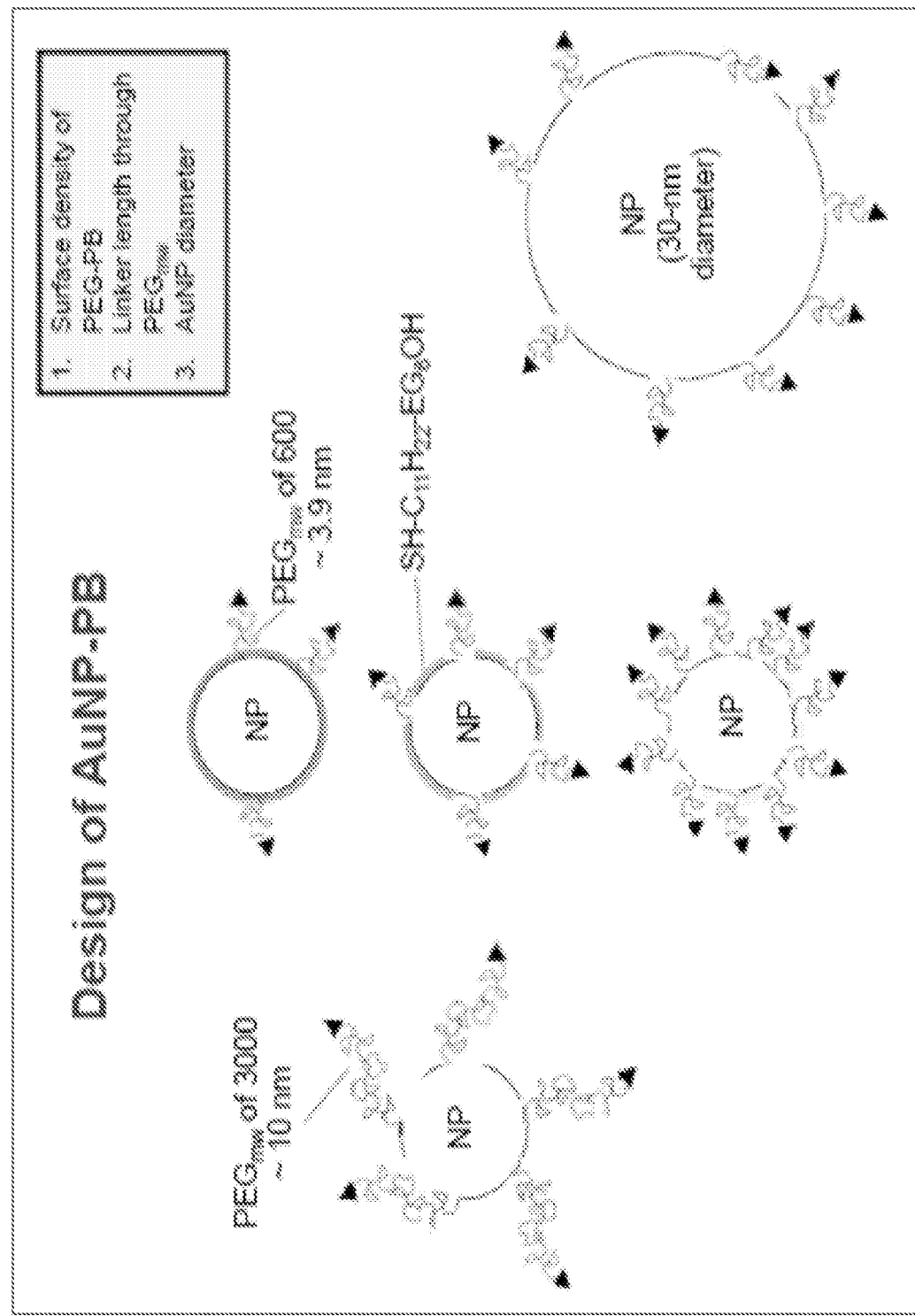
FIG. 4. Schematic depicting the flexibility of the materials that find use in embodiments herein.
Figure 5:
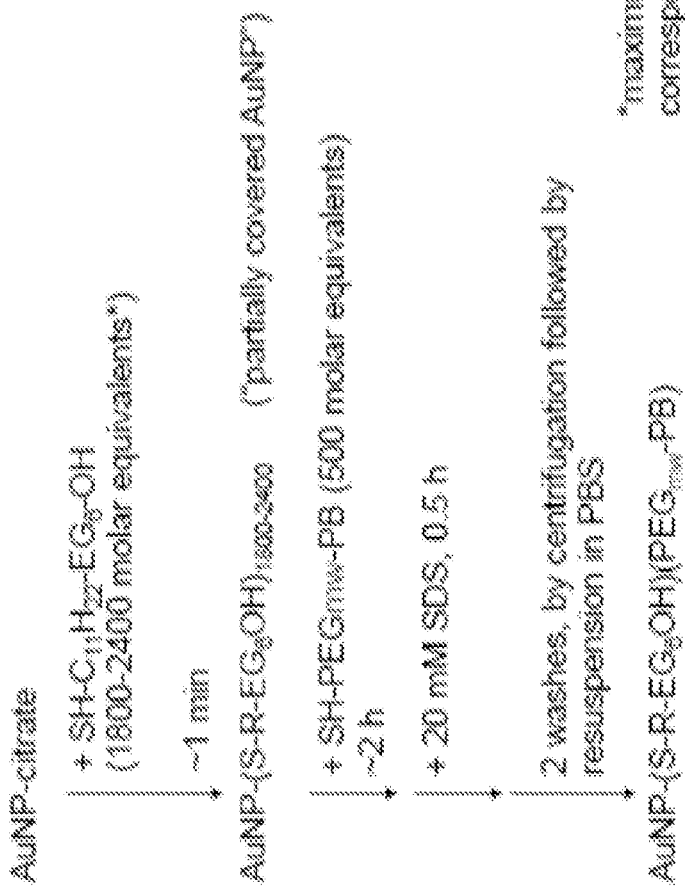
FIG. 5. Exemplary synthesis scheme.
Figure 6:
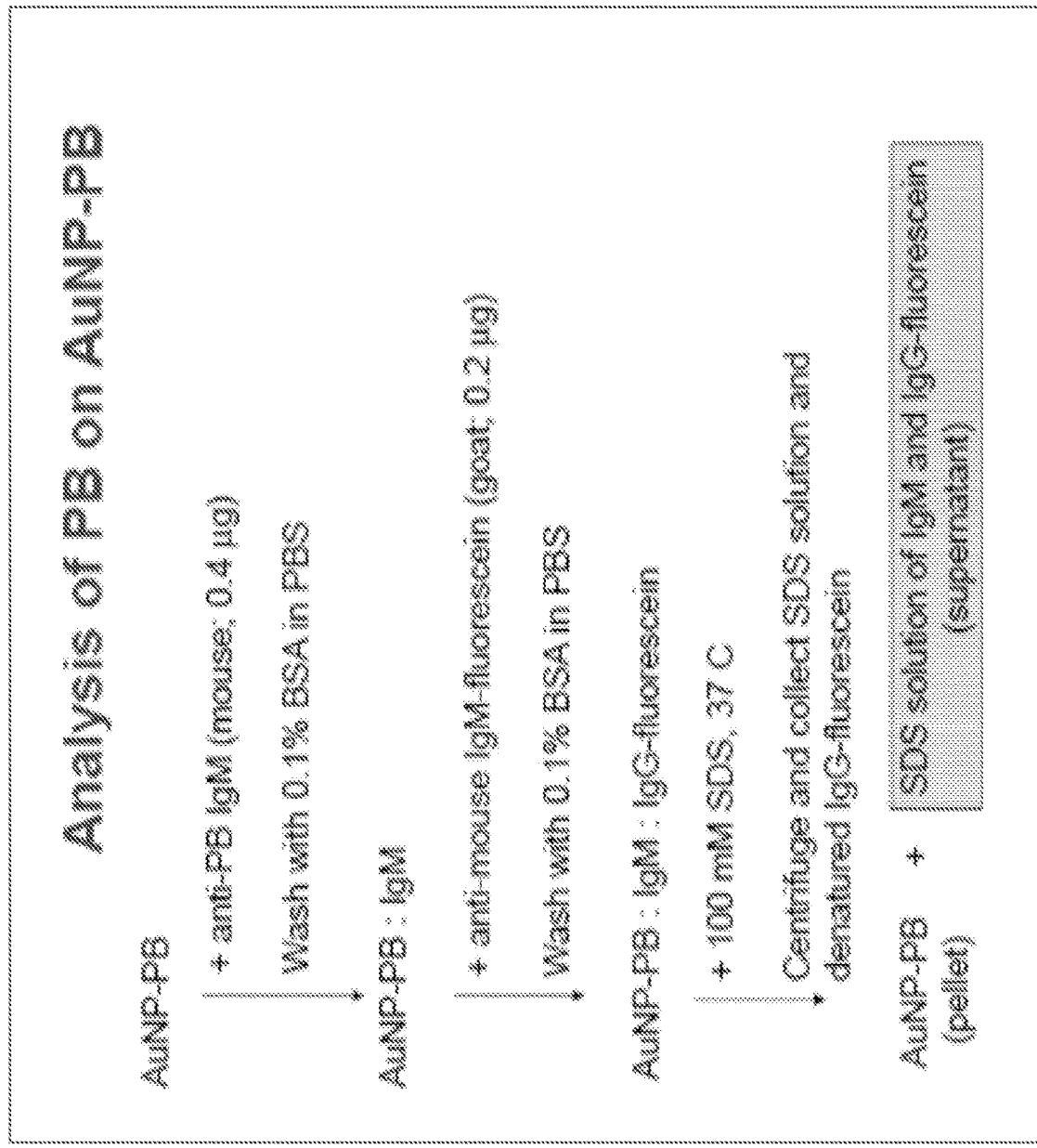
FIG. 6. Exemplary analysis scheme.
Figure 7:
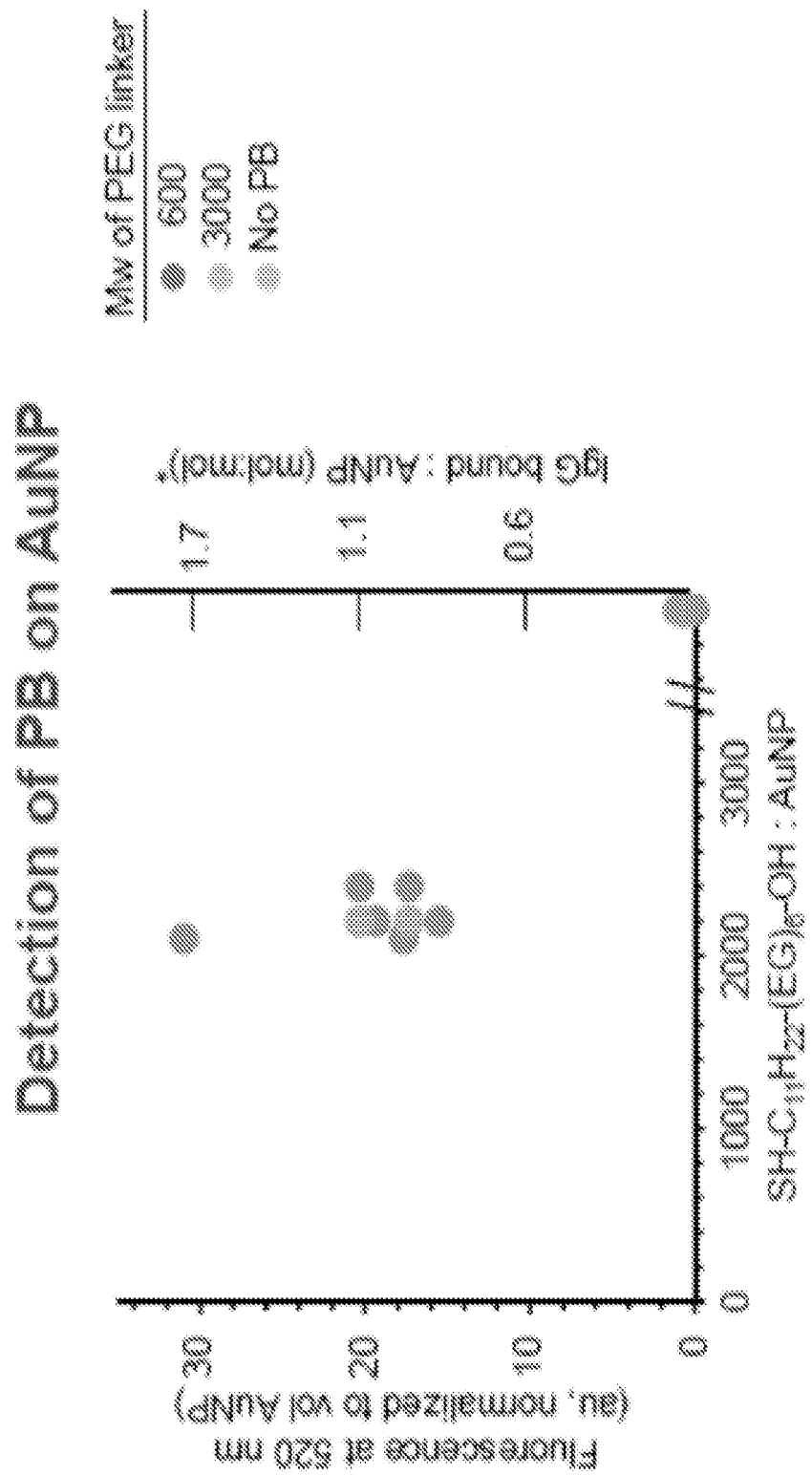
FIG. 7. Graph depicting the effect of the linker: NP ratio on the antibiotic:NP ratio.
Figure 8:
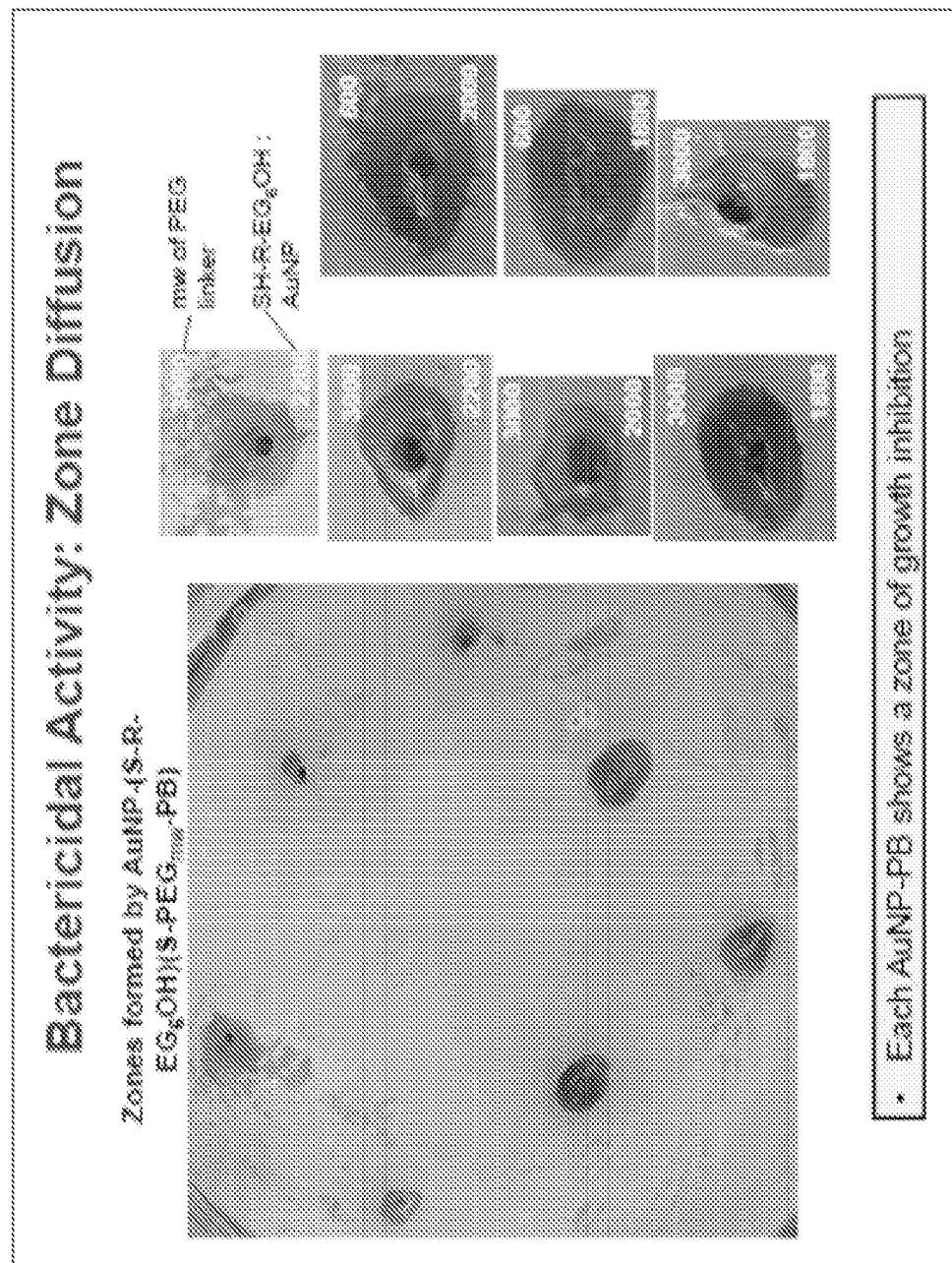
FIG. 8. Images depicting the bactericidal activity of exemplary antibiotic/NP conjugates.
Figure 9:
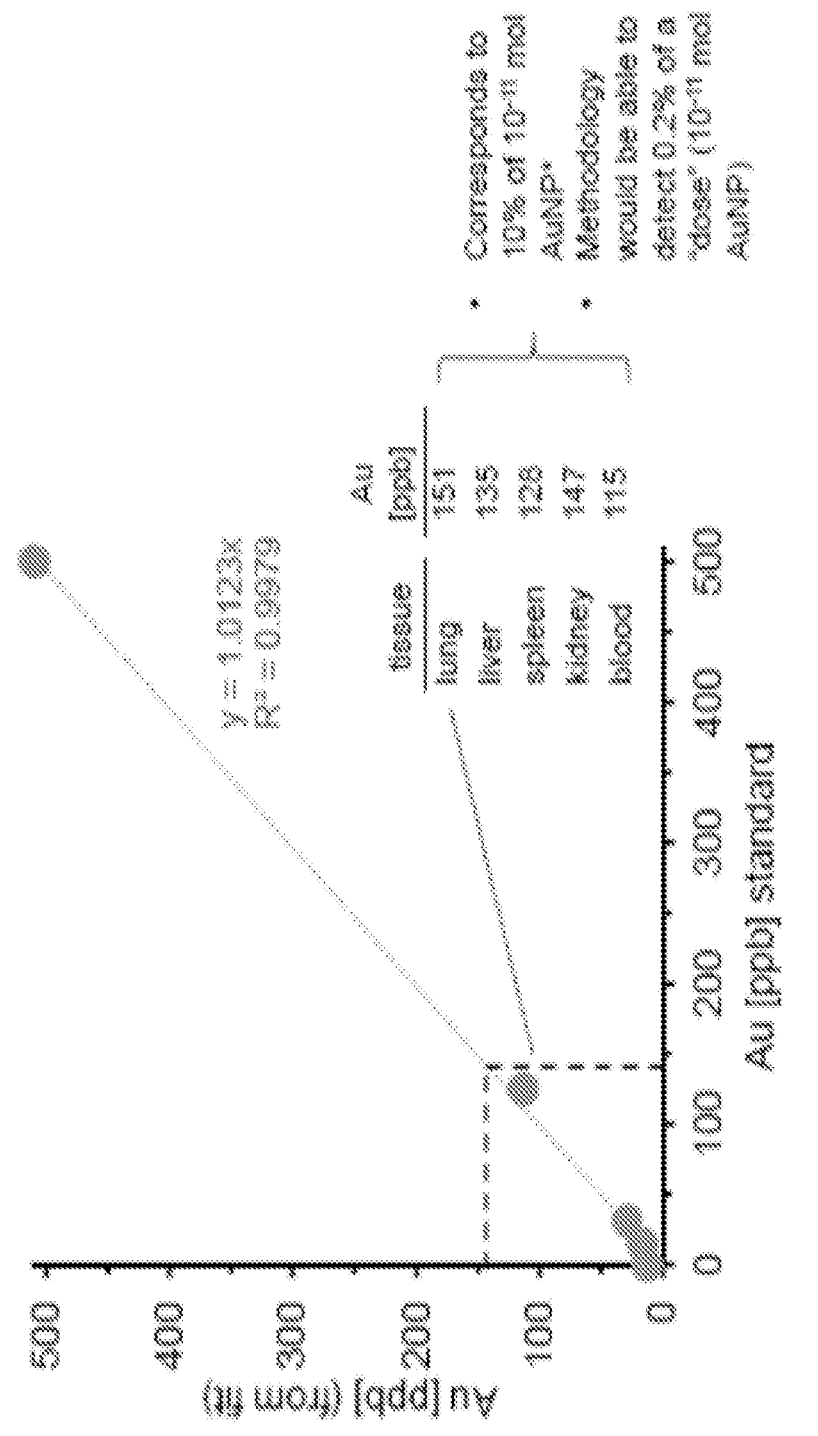
FIG. 9. Graph depicting measurement of accumulation of exemplary antibiotic/NP conjugates in various organs in vivo.
Figure 10:
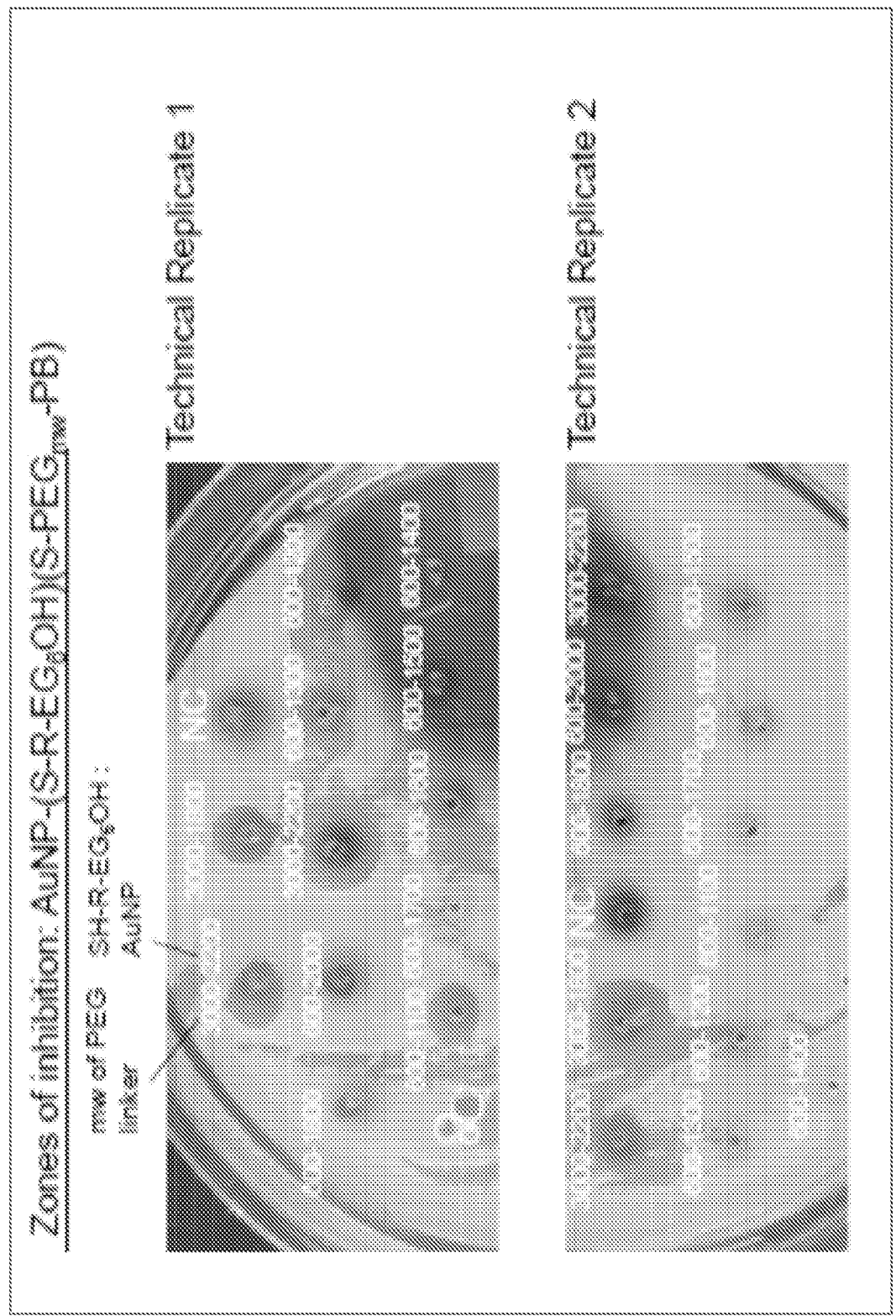
FIG. 10. Images depicting the bactericidal activity of exemplary antibiotic/NP conjugates.
Figure 11:
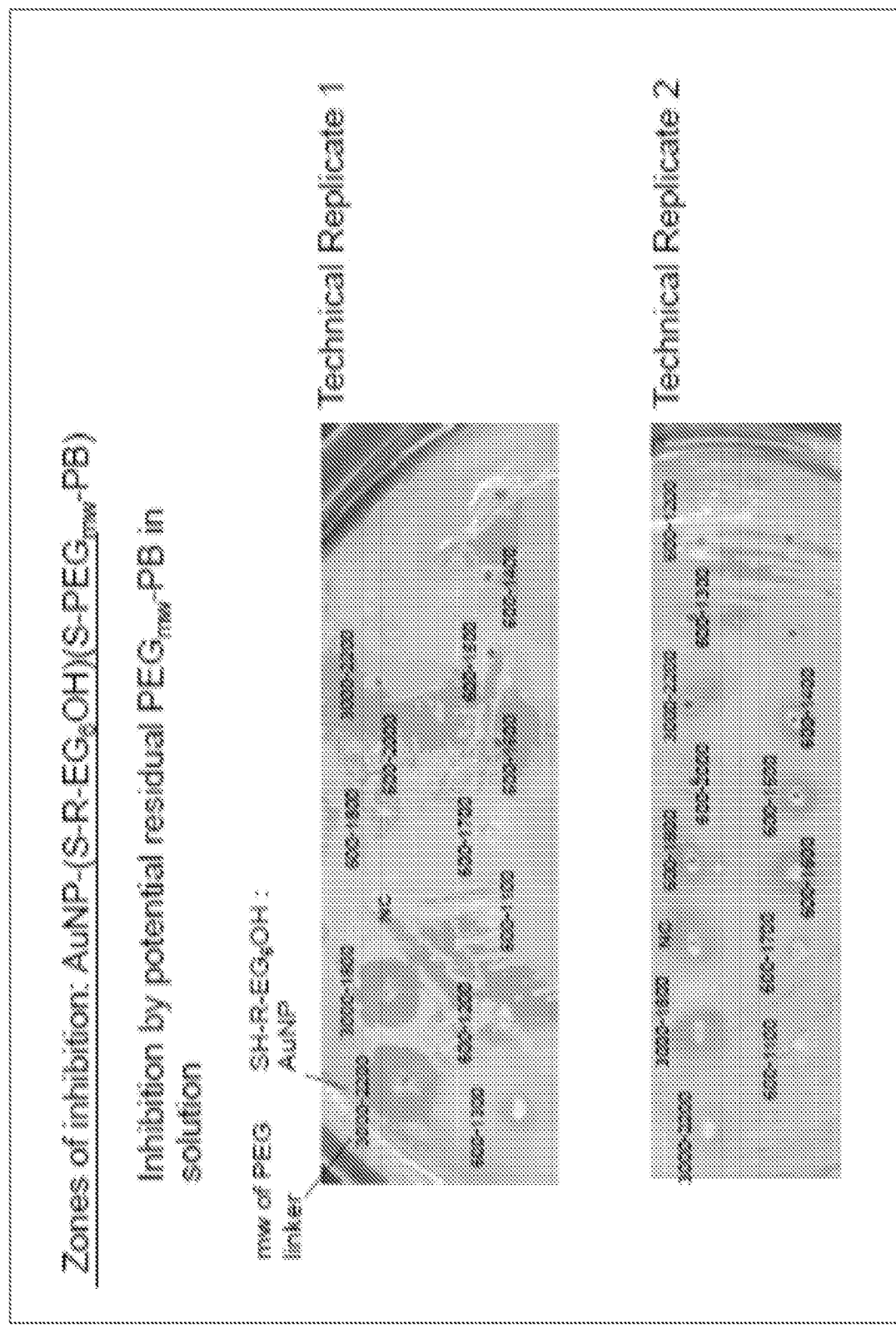
FIG. 11. Images depicting the bactericidal activity of exemplary antibiotic/NP conjugates.
Figure 12:
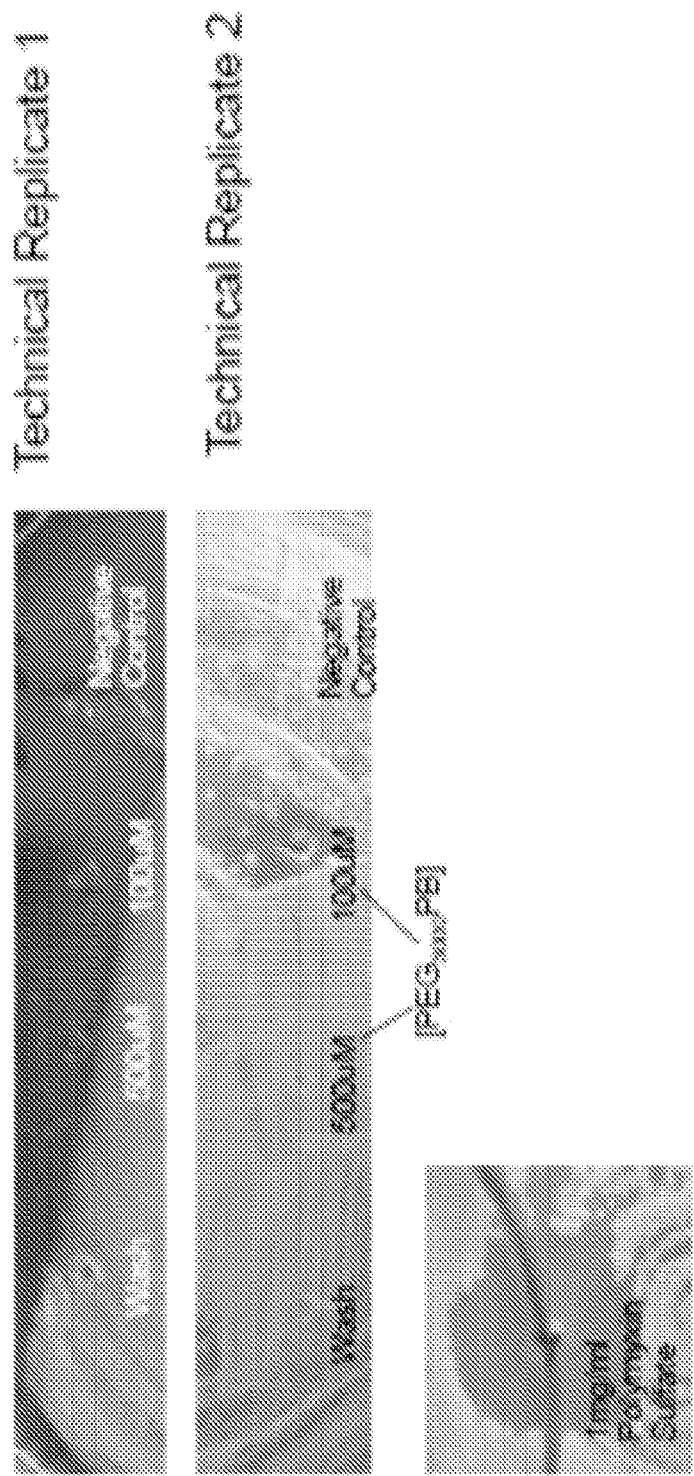
FIG. 12. Images depicting the bactericidal activity of exemplary antibiotic/NP conjugates.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a nanoparticle" is a reference to one or more nanoparticles and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "pharmaceutically acceptable carrier" refers to non-toxic solid, semisolid, or liquid filler, diluent, encapsulating material, formulation auxiliary, or carrier conventional in the art for use with a therapeutic agent for administration to a subject. A pharmaceutically acceptable carrier is non-toxic to recipients at the dosages and concentrations employed and are compatible with other ingredients of the formulation. The pharmaceutically acceptable carrier is appropriate for the formulation employed. For example, if the therapeutic agent is to be administered orally, the carrier may be a gel capsule. A "pharmaceutical composition" typically comprises at least one active agent and a pharmaceutically acceptable carrier.

As used herein, the term "effective amount" refers to the amount of a composition (e.g., pharmaceutical composition) sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., pharmaceutical compositions herein) to a subject or in vivo, in vitro, or ex vivo cells, tissues, and organs. Exemplary routes of administration to the human body can be through the eyes (e.g., intraocularly, intravitrealy, periocularly, ophthalmic, etc.), mouth (oral), skin (transdermal), nose (nasal), lungs (inhalant), oral mucosa (buccal), ear, rectal, by injection (e.g., intravenously, subcutaneously, intratumorally, intraperitoneally, etc.) and the like.

As used herein, the terms "co-administration" and "co-administer" refer to the administration of at least two agent(s) or therapies to a subject. In some embodiments, the co-administration of two or more agents or therapies is concurrent (e.g., in the same or separate formulations). In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "nanoparticle" refers to a particle having dimensions between 1 and 1000 nanometers. A nanoparticle may or may not exhibit one or more size-related properties that differ significantly from those observed in larger particles or bulk materials.

DETAILED DESCRIPTION

Provided herein are antibiotic coated nanoparticles and methods of treating bacterial infection therewith. In particular embodiments, polymyxin B, vancomycin, and/or other antibiotics are linked to nanoparticles (e.g., gold or silica nanoparticles) and utilized for the treatment of bacterial infections. Such antibiotic-coated nanoparticles advantageously concentrate antibiotic exposure at the site of the infection, have increased efficacy and more favorable pharmacokinetic/pharmacodynamic properties compared to conventionally administered antibiotics, limit exposure elsewhere in the host, reduce the development of antibiotic resistance, and prevent adverse effects of antibiotics on uninfected tissues.

Polymyxin B (PB) and polymyxin E (colistin) belong to the class of antimicrobial peptide antibiotics refered to as polymyxins. Despite successful use in the 1960s and 1970s, polymyxins were largely discarded when less toxic alternatives became available. PB kills these gram-negative pathogens by binding to lipopolysaccharide (LPS) and disrupting their membranes. Although PB is one of the few antibiotics to which many of these problematic gram-negative pathogens remain susceptible, its utility in this context continues to be limited by its narrow therapeutic window. In particular, the maximum dose of PB tolerated by patients results in suboptimal efficacy and frequent clinical failures, while further dose escalation is associated with unacceptably high rates of renal toxicity in the form of acute tubular necrosis.

Provided herein are nanoparticle (e.g., Au nanoparticle) conjugated antibiotics (e.g., polymyxins (e.g., polymyxin B) that improve potency through multivalent display of antibiotics and/or limit nephrotoxicity through nanoparticle-controlled tissue localization, and methods of use therefor for the treatment of infections by, for example, gram-negative ESKAPE pathogens. In some embodiments, the surface-exposed antibiotics (e.g., polymyxins (e.g., polymyxin B) target the nanoparticles (e.g., Au nanoparticles) to the outer membrane of the bacteria (e.g., gram-negative bacteria (e.g., ESKAPE bacteria)). In some embodiments, these conjugates provide highly concentrated boluses of LPS-binding antibiotics (e.g., polymyxins (e.g., polymyxin B) delivered to spatially localized patches of bacterial membranes. thereby enhancing antibiotic delivery to the surfaces of pathogens (e.g., gram-negative bacterial pathogens (including those resistant to conventional antibiotics)) and to overwhelm bacterial membrane repair mechanisms. In some embodiments, the diameter of the conjugates provides appropriate distribution to infected tissues, but exclusion from glomerular filtration by the kidney to limit nephrotoxicity. Experiments conducted during development of embodiments herein have demonstrated that gold nanoparticle (e.g., Au nanoparticle) conjugated antibiotics (e.g., polymyxins (e.g., polymyxin B) are bactericidal against gram-negative bacteria in vitro, that they are largely excluded from the kidneys of infected rats, and that they have in vivo activity in a mouse abscess model.

In some embodiments, the conjugates described herein achieved enhanced therapeutic efficacy (e.g., antibiotic efficiency) against the desired pathogens due, at least in part, to the presentation of antibiotics at high density on the surface of a nanoparticle, leveraging the simultaneous and cooperative association of multiple antibiotic units LPS over the localized footprint of a nanoparticle (e.g., 50 nm$^2$ to 500 nm$^2$ (e.g., 50 nm$^2$, 60 nm$^2$, 70 nm$^2$, 80 nm$^2$, 90 nm$^2$, 100 nm$^2$, 110 nm$^2$, 120 nm$^2$, 130 nm$^2$, 140 nm$^2$, 150 nm$^2$, 200 nm$^2$, 300 nm$^2$, 400 nm$^2$, 500 nm$^2$, or ranges therebetween)). This multivalent interaction overwhelms bacterial membrane repair mechanisms, leading to greater susceptibility of the membrane to failure (ref. 13; incorporated by reference in its entirety). With regard to pharmacokinetics (PKs), the conjugates exceed the filtration limit of the kidney (~5.5 nm; ref. 14; incorporated by reference in its entirety), minimizing exposure of renal tubular cells to antibbiotics. Likewise, the conjugates may delay antibioticclearance B, increasing the area under the curve (AUC) (ref 15; incorporated by reference in its entirety), which is the major driver of antibiotic (e.g., PB) efficacy (ref 16; incorporated by reference in its entirety). Since kidney injury is frequently dose limiting (See, e.g., ref 17; incorporated by reference in its entirety), better tolerated conjugates allow administration at higher doses for improved efficacy. In some embodiments, in addition to enhancing efficacy and reducing toxicity, the conjugates here are of a size that is compatible with dispersion in solution and delivery, for example, by intravenous administration (ref. 18; incorporated by reference in its entirety).

In some embodiments, provided herein are surface-functionalized nanoparticles (NPs) displaying antibiotics. In some embodiments, conjugates of nanoparticles and antibiotics are provided. In some embodiments, antibiotics (e.g., polymyxins (e.g., polymyxin B), a polymyxin and one or more additive or synergistic antibiotic (e.g., vancomycin), etc.) are conjugated to a nanoparticle (e.g., Au NP) by a suitable linker (e.g., PEG, or PEG-containing linker). In some embodiments, antibiotic-displaying NPs are provided as a therapeutic agent (e.g., in the methods herein) for the treatment of pathogenic infections, including infections by multidrug-resistant (MDR) bacteria (e.g., *A. baumannii*, CRE, *P. aeruginosa*).

In some embodiments, the antibiotic/NP conjugates herein are provided for the treatment of gram-negative bacterial infections. In some embodiments, antibiotic/NP conjugates for the treatment of gram-negative bacterial infections display one or more polymyxins (e.g., polymyxin B). In some embodiments, antibiotic/NP conjugates for the treatment of gram-negative bacterial infections display one or more polymyxins and one or more additive or synergistic antibiotics (e.g., vancomycin). In some embodiments, the antibiotic/NP conjugates herein are provided for the treatment of gram-positive bacterial infections (e.g. *Staphylococcus aureus, Enterococcus* spp.). In some embodiments, such nanoparticles are decorated with peptidoglycan-binding antibiotics such as vancomycin and beta-lactams.

In some embodiments, provided herein are antibiotic/NP conjugates displaying PB and V (NP-PB-V; shown schematically in FIG. 1). In some embodiments, antibiotic/NP conjugates (e.g., NP-PB-V) display antibiotics with mechanism of action involves association with and disruption of the cell wall of the bacterium. This feature enables antibiotic activity through interfacial contact between the nanoparticle and bacterium; entry into the bacterial cytosol is not required for activity. In some embodiments, antibiotic/NP conjugates (e.g., NP-PB-V) display a combination of antibiotic agents that act upon different components of the cell wall (e.g., PB associates with the lipopolysaccharide (LPS) of the outer membranes while V disrupts the biosynthesis of the peptidoglycan layer). In such embodiments, two essential bacterial structures are attacked simultaneously, thereby enhancing potency and minimizing emergence of resistance. In some embodiments, multiple different antibiotics (e.g., PB and V) are each presented at high surface density (e.g., 0.1 nm$^{-2}$, 0.2 nm$^{-2}$, 0.3 nm$^{-2}$, 0.4 nm$^{-2}$, 0.5 nm$^{-2}$, 0.6 nm$^{-2}$, 0.7 nm$^{-2}$, 0.8 nm$^{-2}$, 0.9 nm$^{-2}$, 1 nm$^{-2}$, 2 nm$^{-2}$, 3 nm$^{-2}$, 4 nm$^{-2}$, 5 nm$^{-2}$, 6 nm$^{-2}$, 7 nm$^{-2}$, 8 nm$^{-2}$, 9 nm$^{-2}$, 10 nm$^{-2}$, or ranges therebetween), thereby enabling multivalent interactions of the antibiotics (e.g., PB and V) at sites of adhesion between nanoparticle and bacterium, leading to enhancement in potency. In some embodiments, the diameter of an antibiotic/NP conjugate is between 10 and 200 nm (e.g., 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, or ranges therebetween). In such embodiments, the antibiotic/NP conjugate maximizes the pharmacokinetic disposition of the conjugate compared to profiles free antibiotics (e.g., PB or V) administered intravenously as individual drugs. In some embodiments, the co-presentation of multiple antibiotics (e.g., PB and V) on a nanoparticle at surface enhances the activity of the antibiotic combination.

In some embodiments, the conjugates herein (while being nanoparticles themselves) comprise a nanoparticle core ("the nanoparticle") and one or more pendant antibiotics ("the antibiotic") linked to the NP core by one or more linker moieties ("the linker").

In some embodiments, nanoparticles may be of any suitable material (e.g., not limited to gold and/or silica).

In some embodiments, the nanoparticles are biodegradable nanoparticles. In some embodiments, the biodegradable nanoparticles comprise a material chosen from natural polymers, such as polysaccharides and proteins, synthetic biodegradable polymers, variants or derivatives thereof, and combinations thereof. Non-limiting examples of suitable polysaccharides include starch, amylose, amylopectin, cellulose, arabinoxylan, chitin, chitinosan, pectin, alginate, carageenan, dextrin, gums (e.g., arabic gum, gellan gum, guar gum, locust bean gum, xanthan gum), or combinations thereof. Examples of suitable proteins include but are not limited to serum albumin, egg albumin, casein, collagen, gelatin, soy protein, whey protein, zein, or combinations thereof. Non-limiting examples of suitable synthetic biodegradable polymers include poly-lactide, poly-D-L-glycolide, poly-D-L-lactide-coglycolide, poly-ε-caprolactone, polyalkylenglycol (e.g., polyethyleneglycol), 1,3-propanediol, 1,4-butanediol, polycyanoacrylate, polyalkylcyanoacrylate, polyanhydride, polyorthoester, or combinations thereof. The polysaccharide, protein, or synthetic biodegradable polymer may be derivatized with one or more groups chosen from alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

In some embodiments, the nanoparticles are biostable (e.g., not biodegradeable) nanoparticles. In some embodiments, the biostable nanoparticles comprise a material chosen from one or more metal, such as silver, gold, nickel, copper, titanium, silicon, galadium, palladium, platinum, chromium, or metal alloys, composites or amalgams thereof.

In some embodiments, the nanoparticle is of any suitable size to properly display a suitable number and density of antibiotics, and/or to reduce toxicity and/or clearance of the antibiotics by the kidneys. For example, in some embodiments, the natoparticle is In some embodiments, nanoparticles are between 10 and 200 nm in diameter (e.g., 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, or ranges therebetween)

In some embodiments, any suitable antibiotics (or combinations of antibiotics) for the treatment of any bacterial infection (e.g., gram negative, gram positive) are within the scope herein. For example, in some embodiments, the antibiotic is selected from chloramphenicol, erythromycin, lincomycin, fusidic acid, streptomycin, an aminoglycoside antibiotic, a tetracycline, a polymyxin, fosfomycin, vancomycin, ristocetin, bacitracin, gramacidin, a penicillin, peptidoglycan-binding antibiotics, a cephalosporin, etc.

In some embodiments, conjugates display one or more antibiotics that are effective in the treatment of gram-negative bacteria. In some embodiments, conjugates display one or more antibiotics that are effective in the treatment of gram-positive bacteria. In some embodiments, conjugates display one or more antibiotics that target the exterior (e.g., cell wall) of a bacteria (e.g., the antibiotic does not need to enter the bacteria). In some embodiments, conjugates display two or more antibiotics that function via distinct mechanisms. In some embodiments, conjugates display one or more aminoglycosides, ansamycins, carbacephems, carbapenems, cephalosporins, glycopeptides, lincosamides, lipopeptide, macrolides, monobactams, nitrofurans, oxazolidinones, penicillins, polypeptides, quinolones, sulfonamides, tetracyclines, drugs against mycobacteria, etc. Exemplary antibiotics that may find use in some embodiments include, but are not limited to: amikacin, gentamicin, kanamycin, neomycin, netilmicin, streptomycin, tobramycin, paromycin, geldanamycin, herbimycin, loracarbef, ertapenem, doripenem, imipenem, meropenem, cefaclor, cefamandole, cefotoxin, cefprozil, cefuroxime, cefixime, cefdinir, cefditoren, cefpodoxime, ceftazidime, ceftibuten, ceftizoxime, ceftriaxone, cefepime, ceftobirprole, vancomycin, azithromycin, clarithromycin, dirithromycin, erythromycin, roxithromycin, troleandomycin, telithromycin, spectinomycin, aztreonam, amoxicillin, ampicillin, azociling, carbenicillin, cloxacillin, dicloxacillin, flucloxacillin, mezlocillin, meticillin, nafcillin, oxacillin, peperacillin, ticarcillin, bacitracin, colistin, polymyxin B, ciprofloxacin, clavulanic acid, enoxacin, gatifloxacin, levofloxacin, lomefloxacin, moxifloxacin, nonfloxacin, ofloxacin, trovafloxacin, grepafloxacin, sparfloxacin, AL-15469A, AL-38905, OP-145, afenide, prontosil, sulfacetamide, sulfamethiazole, sulfanamide, sulfasalazine, sulfisoxazole, trimethoprim, cotrimoxazole, demeclocycline, doxycycline, minocycline, oxytetracycline, tetraycline, linezolid, arsogebanubem chloramphenicol, clindamycin, lincomycin, ethambutol, fosfomycin, fusidic acid, furazolidone, isoniazid, linezolid, metronidazole, mupirocin, nitrofurantoin, rifampicin, thamphenicol, tinidazole, amoxicillin+clavulanic acid, Maximin H5, Dermcidin, Cecropins, andropin, moricin, ceratotoxin, melittin, Magainin, dermaseptin, bombinin, brevinin-1,esculentins and buforin II, CAP 18, LL37, abaecin, apidaecins, prophenin, indolicidin, brevinins, protegrin, tachyplesins, defensins, drosomycin, alamethicin, pexiganan or MSI-78, MSI-843, MSI-594, polyphemusin, colicin, pyocin, klebicin, subtilin, epidermin, herbicolacin, brevicin, halocin, agrocin, alveicin, carnocin, curvaticin, divercin,enterocin, enterolysin, erwiniocin, glycinecin, lactococin, lacticin, leucoccin, mesentericin, pediocin, plantaricin, sakacin, sulfolobicin, vibriocin, warnerinand, nisin, or a salt or cocrystal, or prodrug or solvate thereof, or a combination thereof.

In some embodiments, in addition to an antibiotic (or in place of an antibiotic), the conjugates herein displa one or more non-antibiotic antimicrobials. In some embodiments, the antimicrobial is an antifungal agent. Exemplary antifungals that may find use in some embodiments include, but are not limited to: amrolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopirox olamine, haloprogin, tolnaftate, undecylenate, clioquinol, and combinations thereof. In some embodiments, the antimicrobial is an antiparasitic. Exemplary antiparasitics that may find use in some embodiments include, but are not limited to:amitraz, amoscanate, avermectin, carbadox, diethylcarbamizine, dimetridazole, diminazene, ivermectin, macrofilaricide, malathion, mitaban, oxamniquine, permethrin, praziquantel, prantel pamoate, selamectin, sodium stibogluconate, thiabendazole, and combinations thereof.

In some embodiments, a conjugate herein displays a polypeptide antibiotic. In some embodiments, the polypeptide antibiotic is a polymyxin. In some embodiments, the polymyxin is polymyxin B:

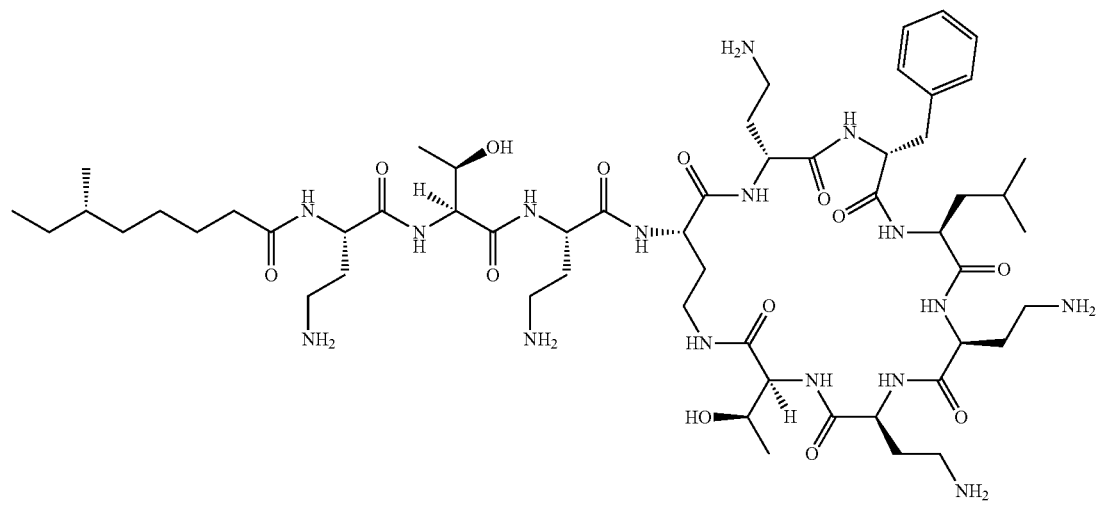
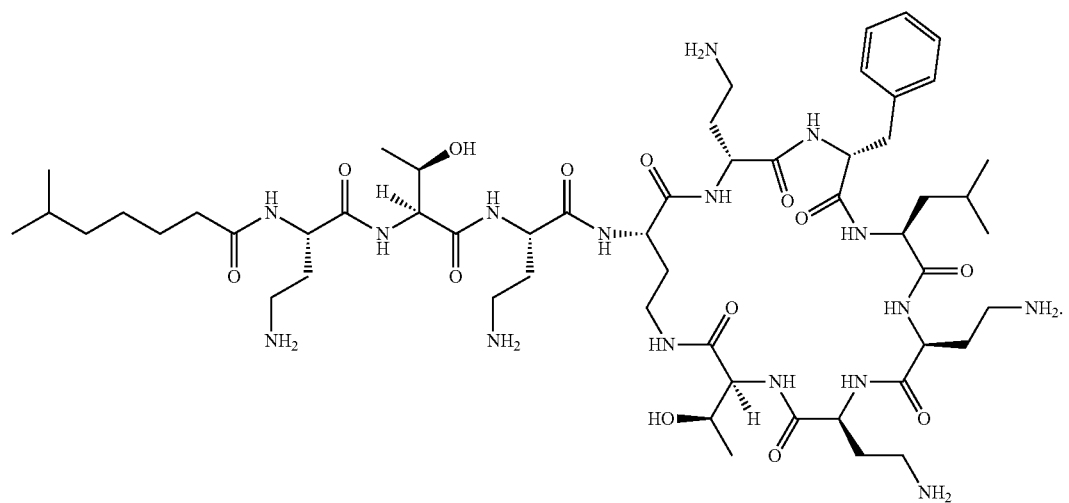

In some embodiments, the polymyxin is polymyxin E (colistin):

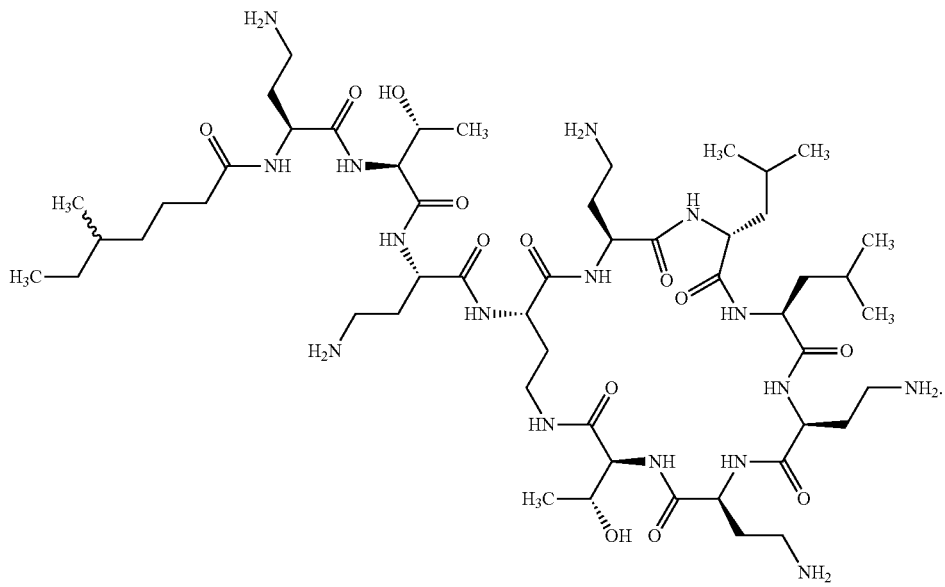 [SMILES: CCC(C)CCCC(=O)N[C@@H](CCN)C(=O)N[C@H](C(=O)N[C@@H](CCN)C(=O)N[C@H]1CCNC(=O)[C@H]([C@@H](C)O)NC(=O)[C@H](CCN)NC(=O)[C@H](CCN)NC(=O)[C@H](CC(C)C)NC(=O)[C@@H](CC(C)C)NC(=O)[C@H](CCN)NC1=O)[C@@H](C)O]

In some embodiments, a conjugate herein displays a glycopeptide antibiotic. In some embodiments, the glycopeptide antibiotic is vancomycin:

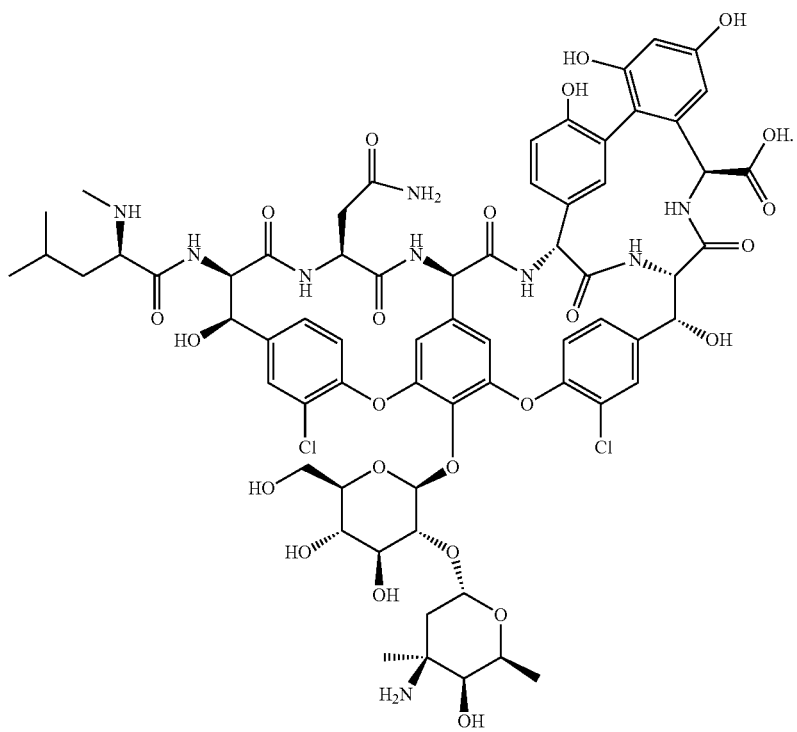 [SMILES: CN[C@H](CC(C)C)C(=O)N[C@H]1C(=O)N[C@@H](CC(N)=O)C(=O)N[C@H]2C(=O)N[C@H]3C(=O)N[C@H](C(=O)N[C@H](C(=O)O)c4cc(O)cc(O)c4-c4cc3ccc4O)[C@H](O)c3ccc(c(Cl)c3)Oc3cc2cc(c3O[C@@H]2O[C@H](CO)[C@@H](O)[C@H](O)[C@H]2O[C@H]2C[C@](C)(N)[C@H](O)[C@H](C)O2)Oc2ccc(cc2Cl)[C@H]1O]

In some embodiments, a conjugate herein displays polymyxin B and vancomycin.

In some embodiments, conjugates herein comprise two or more antibiotics. In some embodiments, the antibiotics target separate bacteria or classes of bacteria (e.g., gram-negative and gram-positive). In some embodiments, the antibiotics are useful against a single bacteria, but via different mechanisms.

In some embodiments, a first antibiotic or compound (e.g., polymyxin) linked to the nanoparticle functions as a targeting moiety, bringing the nanoparticle to the bacterium. In some embodiments, a second antibiotic or compound linked to the nanoparticle functions to kill the bacterium. In some embodiments, the antibiotic-linked nanoparticles are delivery vehicles that bring other antibiotics to the bacterial target.

In some embodiments, a suitable linker connects the nanoparticle to the antibiotic. In some embodiments, the linker is covalently or non-covalently bound to the antibiotic. In some embodiments, the linker is covalently or non-covalently bound to the nanoparticle. In some embodiments, the linker is covalently bound to the antibiotic and comprises a functional group (e.g., thiol) for stable association with the nanoparticle. In some embodiments, linker provides solubility, flexibility, distance, etc.

In some embodiments, the linker is a non-peptide linker. In some embodiments, the linker provides a functional or reactive group (e.g., alkene, alkyne, azide, thiol, maleimide etc.) attachment to the nanoparticle. In some embodiments, the linker is a substantially linear chain of $CH_2$, O, $(CH_2)_2O$, $O(CH_2)_2$, NH, and C=O groups. In some embodiments, the linker comprises a PEG group. In some embodiments, a linker further comprises additional bioactive groups, substituents, branches, etc. In some embodiments, a non-peptide linker is of any suitable length (e.g., 4-50 molecular bonds in length (e.g., 4, 5, 6, 7, 8, 9, 10, 12, 14, 16, 18, 20, 25, 30, 35, 40, 45, 50, or ranges therebetween)).

In some embodiments, the linker is a peptide linker. In some embodiments, a peptide linker is of any suitable length (e.g., 2-20 amino acids in length (e.g., 2, 3, 4, 5, 6, 7, 8, 9, 10, 12, 14, 16, 18, 20, or ranges therebetween)). In some embodiments, a peptide linker comprises any sequence of natural amino acids, unnatural amino acids, and/or amino acid analogs.

In some embodiments, a linker comprises peptide and non-peptide portions.

In some embodiments, any suitable linker may be employed for attachment of the antibiotic to the nanoparticle. Accordingly, according to some embodiments, the biodegradable linker is a pH-sensitive linker or an enzymatically-cleavable linker. Suitable linkers include, but are not limited to, alkyl chains; alkyl chains optionally substituted with one or more substituents and in which one or more carbon atoms are optionally interrupted by a nitrogen, oxygen and/or sulfur heteroatom. Other suitable linkers include amino acids and/or oligopeptides. In some embodiments, a linker comprises a carbon chain, optionally substituted with known organic functional groups. In some embodiments, a linker comprises PEG (e.g., $(OCH_2)_n$, wherein n is 2 to 100 (e.g., 2, 3, 4, 5, 6, 7, 8, 9, 10, 12, 14, 16, 18, 20, 25, 30, 35, 40, 45, 50, 60, 70, 80, 90, 100, or ranges therebetween).

In some embodiments, antibiotics are conjugated to the surface of nanoparticles, for example, via a linker, by any suitable chemistry. For example, in some embodiments, a linker comprises a thiol group at one terminus and an antibiotic at the other terminus; in such embodiments, the linker associates with, for example, a gold nanoparticle, via Au/thiol chemistry. In some embodiments, a nanoparticle is surface-functionalized to display one or more functional groups or moieties for attachment of linker/antibiotics. Exemplary functional groups or moieties include: alkene, alkyne, azide, thiol, maleimide, streptavidin, biotin, carboxylic acid, etc. Chemistries for attaching functional groups on linkers to nanoparticles or functionalized surfaces thereof are understood in the field.

In some embodiments, the antibiotic/NP conjugates described herein find use in the treatment of bacterial infections.

In some embodiments, methods are provided herein for the treatment of pathogenic gram-negative bacterial infections. In some embodiments, methods and compositions are provided for the treatment of respiratory infections caused by, for example, *Klebsiella pneumoniae, Legionella pneumophila, Pseudomonas aeruginosa*, etc. In some embodiments, methods and compositions are provided for the treatment of urinary tract infections caused by, for example, *Escherichia coli, Proteus mirabilis, Enterobacter cloacae, Serratia marcescens*, etc. In some embodiments, methods and compositions are provided for the treatment of gastrointestinal infections caused by, for example, *Helicobacter pylori, Salmonella enteritidis, Salmonella typhi*, etc. In some embodiments, methods and compositions are provided for the treatment of hospital-acquired infections caused by, for example, *Acinetobacter baumannii*, etc. In some embodiments, bacteria are drug resistant (e.g., MDR).

In some embodiments, methods are provided herein for the treatment of pathogenic gram-positive bacterial infections. In some embodiments, methods and compositions are provided for the treatment of infection by *Streptococcus, Staphylococcus, Corynebacterium, Listeria, Bacillus, Clostridium*, etc.

Three gram-negative bacteria are widely recognized as particularly problematic with respect to multi-drug resistance are *Pseudomonas aeruginosa* (PA), *Acinetobacter baumannii* (AB), and *Klebsiella pneumoniae* (KP). They have been identified as members of the "ESKAPE" group of organisms (ref. 2; incorporated by reference in its entirety), and the CDC has placed these three bacteria in its top two antibiotic-resistance "Threat" categories (ref 3; incorporated by reference in its entirety). In some embodiments, the compositions and methods described herein find use in the treatment of infections by gram-negative ESKAPE pathogens, such PA, AB, and KP.

Embodiments herein provide pharmaceutical compositions (e.g., comprising the antibiotic/NP conjugates herein). The pharmaceutical compositions may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration (e.g., to tissues, wounds, organs, etc) may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions include, but are not limited to, solutions and emulsions. These compositions may be generated from a variety of components that include, but are not limited to, preformed liquids, self-emulsifying solids and self-emulsifying semisolids.

The pharmaceutical formulations herein, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions herein may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the active agents of the formulation.

Dosing is dependent on severity and responsiveness of the infection to be treated, with the course of treatment lasting from several days to several months, or until a the infection is cleared or a diminution of the infection is achieved. In some embodiments, treatment is administered in one or more courses, where each course comprises one or more doses per day for several days (e.g., 1, 2, 3, 4, 5, 6) or weeks (e.g., 1, 2, or 3 weeks, etc.). In some embodiments, courses of treatment are administered sequentially (e.g., without a break between courses), while in other embodiments, a break of 1 or more days, weeks, or months is provided between courses. In some embodiments, treatment is provided on an ongoing or maintenance basis (e.g., multiple courses provided with or without breaks for an indefinite time period). Optimal dosing schedules can be calculated from measurements of drug accumulation in the body of the patient. The administering clinician can readily determine optimum dosages, dosing methodologies and repetition rates.

In some embodiments, dosage is from 0.01 µg to 100 g per kg of body weight, and may be given once or more daily, weekly, monthly or yearly. The treating clinician can estimate repetition rates for dosing based on measured residence times and concentrations of the drug in bodily fluids or tissues.

EXPERIMENTAL

Example 1

Figure 13:
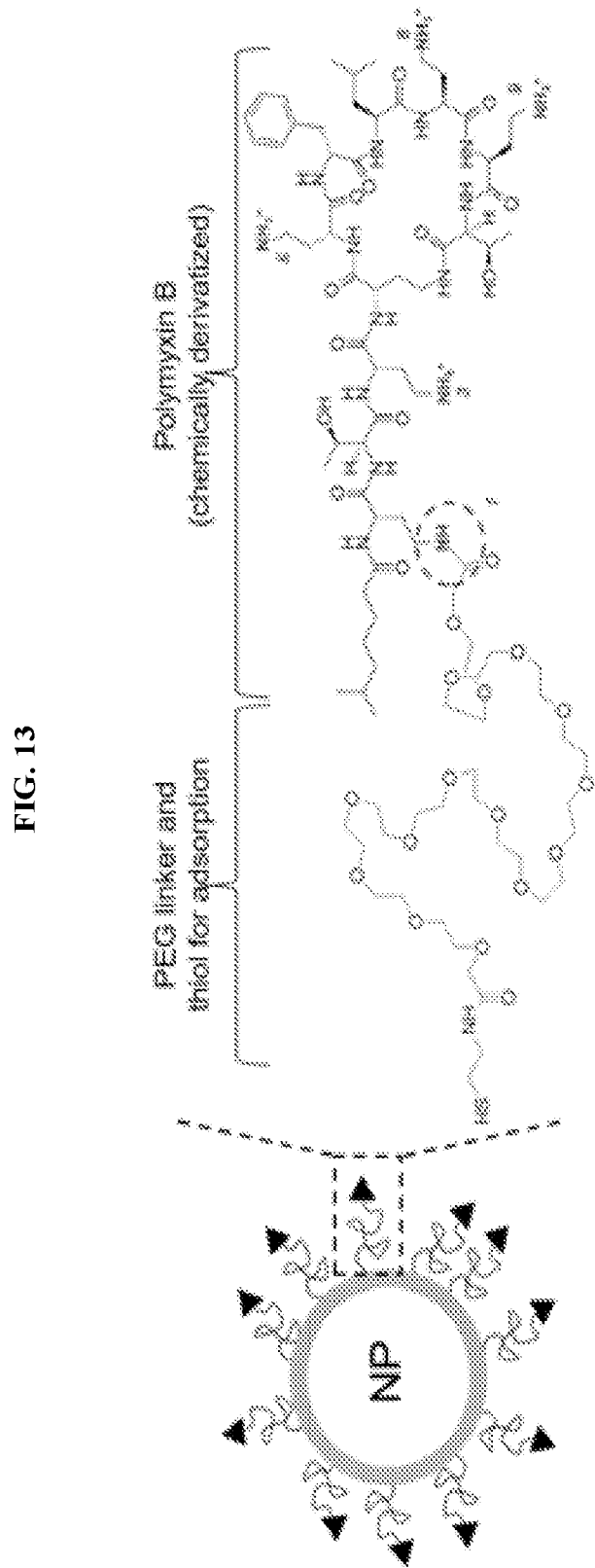
FIG. 13. Schematic showing a nanoparticle scaffold for the polyvalent presentation of PB; of a nanoparticle core decorated with derivatives of PB (left). Chemically derivatized PB is shown with diaminobutyric acid (DAB) residues. The structure shows PEG (Mn~600 g/mol) as the linker with conjugation to DAB1 via amide bond (in the dashed circle). Gray border on the NP represents a SAM presenting maleimide groups.

Synthesis of a Gold Nanoparticle Polymyxin B Conjugate (AuNP-PB) with Bactericidal Activity Against Gram-Negative ESKAPE Pathogens The modular structure and synthesis of AuNP-PB provides for rapid optimization of compounds. AuNP—PB comprises of a AuNP core, flexible linker, and PB (FIG. 13).

An exemplary synthetic route has been established for AuNP-PB using the method of Weinstein (ref. 38; incorporated by reference in its entirety)(FIG. 13). 13-nm AuNP were used. The stoichiometry of PB to AuNP was estimated to be ~225:1 (corresponding to a surface density of 0.17 PB per $nm^2$) based on an analysis of the depletion of the PB-linker conjugate from reaction mixtures with AuNP. A negative-control AuNP lacking PB ("AuNP-NC") was also synthesized. To generate AuNP-NC with the same approximate mass as AuNP-PB, it was functionalized at the surface with poly(ethylene glycol) ($M_n$=2,000), which has the same approximate molecular weight as the sum of the PB (1,200 g/mol) and PEG (600 g/mol) used to generate AuNP-PB.

Figure 14:
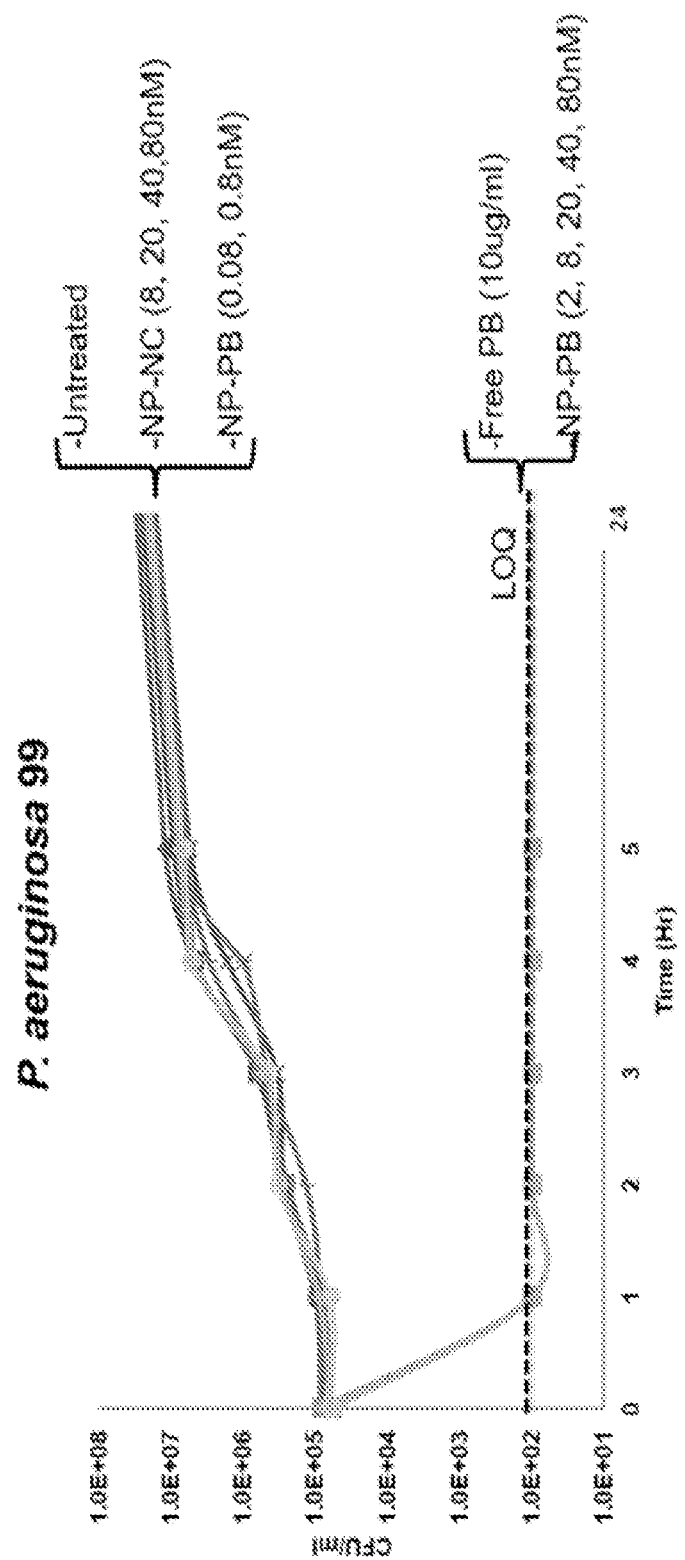
FIG. 14. In vitro killing of PA strain PA99 by AuNP-PB.

Experiments conducted during development of embodiments herein demonstrate the ability of AuNP-PB to kill PA. PA clinical isolate PA99 (ref 39; incorporated by reference in its entirety) was incubated with AuNP-PB and AuNP-NC over a range of concentrations (0.08-80.0 nM of nanoparticles, corresponding to 0.02-22 µg/mL of PB). Concentrations of ≥2 nM AuNP-PB (corresponding to ~0.5 µg/mL PB) resulted in no CFU recovery (FIG. 14). In a separate experiment, it was demonstrated that medium previously incubated with AuNP-PB did not kill PA99 bacteria, demonstrating that PB was not being released from AuNP-PB in amounts capable of accounting for the bactericidal effects observed in FIG. 14. These results show the capacity of AuNP-PB to kill PA99 with a potency that is comparable to that of free PB (the MIC of free PB for PA is 0.5-1.0 µg/mL (ref. 16; incorporated by reference in its entirety)). This equivalent activity was obtained without any attempt to optimize AuNP-PB.

Synthesis of Homogenous Defined AuNP-PB

Figure 15:
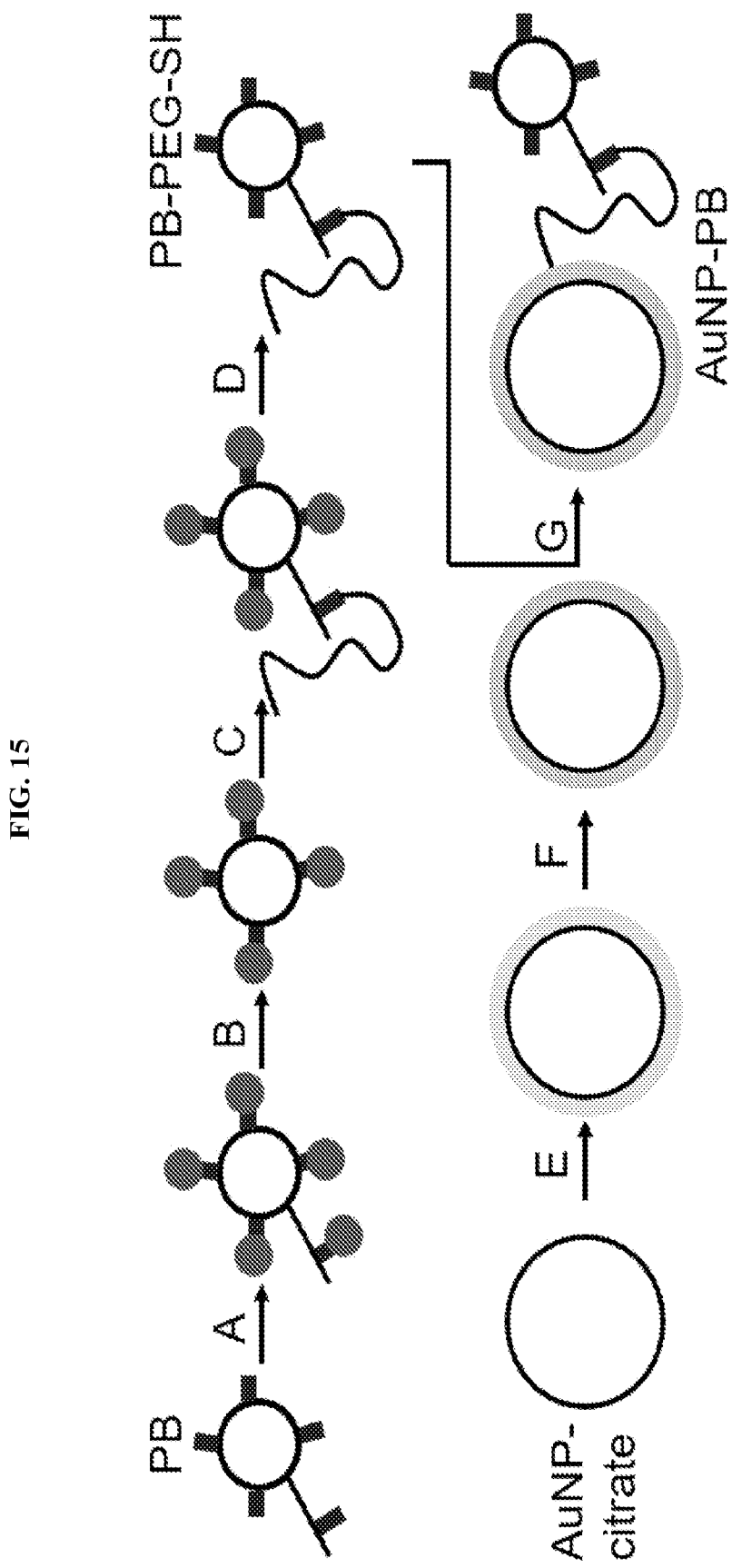
FIG. 15. Exemplary synthetic route to AuNP-PB, via building blocks of PB-PEG-SH and SAM-modified AuNPs. A) Protection of DAB residues with TROC; B) Selective cleavage of DAB1 residue; C) Coupling of DAB1-PEG-SH to NH2 of Thr2; D) Deprotection of TROC; E) Formation of SAMs by adsorption of functionalized alkanethiolates (NHS ester) and reaction with 4,7,10-trioxa-1,13-tridecanediamine; F) Modification of AuNP surface with succinimidyl 4-(p-maleimidophenyl)butyrate; G) Reaction of PB-PEG-SH with maleimide-activated AuNP surfaces.

PB contains 5 positively charged diaminobutyric acid (DAB) residues that play an important role in PB binding to LPS (FIG. 13). One of these five DAB residues was acylated to attach PB to PEG-SH to form PB-linker conjugates (PB-PEG-SH) (ref. 38; incorporated by reference in its entirety). This synthesis, however, provides limited control over which DAB is acylated (although the majority of reactions are predicted to occur at DAB1 and DAB5 (ref. 38; incorporated by reference in its entirety)), and a regioselective mixture of compounds is generated. PB-PEG-SH conjugates are synthesized that are modified exclusively at DAB1. Such a defined homogenous AuNP-PB compound (rather than a mixture of DAB-linked compounds) minimizes the risk of off-target toxicities and provides an avenue for improved potency. The regiochemistry of acylation can have a substantial impact on the activity of PB due to its effects on local charge and sterics (ref. 40; incorporated by reference in its entirety). Dab 1 provides synthetic accessibility and its interactions with the 4'-phosphate group of LPS lipid A are redundant to DAB5 (ref. 40; incorporated by reference in its entirety), resulting in minimal impact on activity from modification at this position (ref. 40; incorporated by reference in its entirety). An approach is used to regiospecifically generate AuNP-PB linked specifically through DAB1, (ref. 41; incorporated by reference in its entirety)(FIG. 15). These PB-PEG-SH molecules are then be reacted with 13-nm AuNP at a surface density of ~0.16 PB per nm$^2$.

The chemical functional group linking the NH$_2$ group of DAB1 to PEG influence the bactericidal activity of PB-PEG-SH (refs. 38,40; incorporated by reference in their entireties). Experiments are conducted during development of embodiments herein to investigate different conjugation chemistries, for example: acylation with the NETS-ester of PEG; reductive amination using aldehyde-functionalized PEG; alkylation with propargyl bromide and subsequent click reactions with azide-functionalize PEG, etc. Acylation generates an amide, and thereby eliminates the electrostatic charge of the NH$_2$ group, the other methods generate amines and in doing so, can conserve the electrostatic charge at the DAB1 residue. The amines generated differ in basicity and may thereby differentiate the electrostatic interactions of PB-PEG-SH produced by these conjugation chemistries.

The antibacterial activity of the synthesized conjugateds (both AuNP-PB and the PB-linker conjugates) are measured in vitro using PA strain PA99 in time-kill assays (see FIG. 14).

Example 2

Demonstration of Superior Pharmacokinetic (PK) and Toxicodynamic (TD) Profiles of AuNP-PB Versus Free PB Clinical PB use is severely limited by nephrotoxicity refs 42,43; incorporated by reference in their entireties), specifically acute tubular necrosis (refs. 44-48; incorporated by reference in their entireties). Therefore, Experiments are conducted during development of embodiments herein perform PK studies and measure the renal toxicities of AuNP-PB* and PB using sensitive urinary biomarkers and histopathology in Sprague-Dawley (SD) rats.

Figure 16:
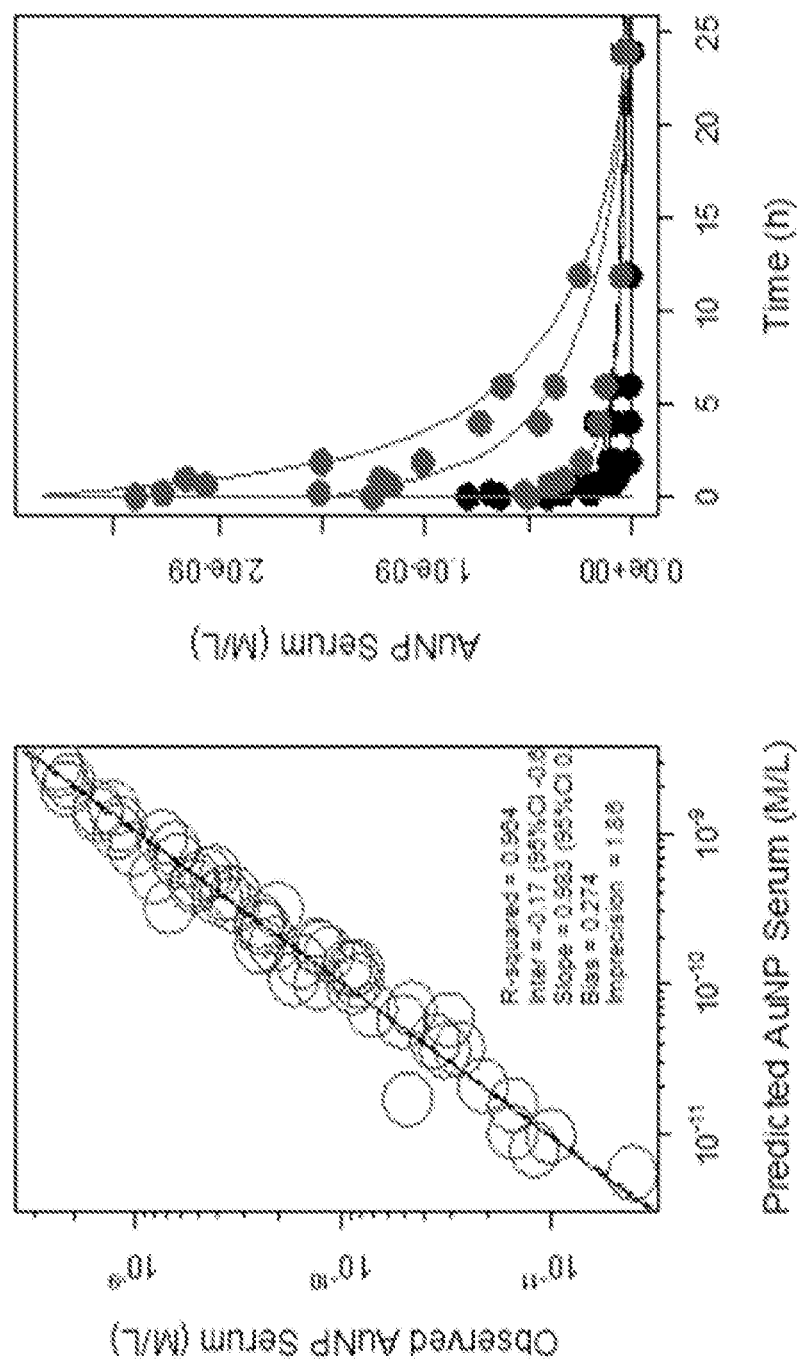
FIG. 16. Pharmacokinetics of AuNP-PB in rats. (A) Plot of observed vs. predicted AuNP concentrations from AuNP and AuNP-PB, 2-compartment PK model (B) PK concentration time plot of AuNP in AuNP-PB and AuNP.

In 24-hr SD rat studies, a single dose of AuNP-PB ($9 \times 10^{-2}$ nmoles of the heterogenous AuNP-PB), PB (12 mg/kg), or AuNP-NC ($3 \times 10^{-2}$ nmoles) was given IV. AuNP-PB demonstrated a mean serum half-life of 6.2 hr (FIG. 16), which is favorable compared to PB alone (mean half-life=1.5 hr (ref. 17; incorporated by reference in its entirety)) in rats. Increasing the half-life will increase AUC compared to PB alone (ref 56; incorporated by reference in its entirety), which is important since increasing the AUC of PB relative to the MIC for the infecting organism increases in situ efficacy (ref 16; incorporated by reference in its entirety). AuNP-PB concentrated 5.6-fold greater in the lungs than the kidneys (data not shown).

Rat PK/TD Model

Male and female SD rats (8 week-old) receive IV PB or AuNP-PB*. Rats (n=5 per gender and drug) will be studied for 1 to 5 days (i.e. 100 total animals). Doses are parameter scaled (ref. 57; incorporated by reference in its entirety) to recapitulate the 90$^{th}$ percentile for human exposures (ref. 58; incorporated by reference in its entirety). Tissues (i.e. lung, spleen, liver, kidneys, thigh) and blood samples are collected and homogenized. AuNP in homogenates are measured by digestion with aqua regia followed by quantitative elemental analysis of gold by inductively coupled plasma mass spectrometry (ICP-MS). Concentrations of PB are analyzed by releasing PB from AuNP by oxidation with iodine and analysis of PB by immunoassay. Urine biomarkers for PB-induced renal toxicity (KIM-1, αGST, NGAL, albumin, clusterin, and Osteopontin) (ref. 51; incorporated by reference in its entirety) are collected via metabolic cage(ref. 59). Histopathology is scored using standard endpoints (ref 60; incorporated by reference in its entirety).

PK Model Fitting and Statistical Analysis Plan

Multiple physiologically relevant compartmental models are constructed using differential equations in Pmetrics for R (refs. 59, 61-75; incorporated by reference in their entireties). Bayesian posteriors classify individual rat PK exposures, parameters (e.g. clearance), and tissue biodistribution constants. Analyses compare urinary biomarker concentrations and kidney histopathology scores by groups (i.e. treatment group, days of therapy, gender, etc.).

Cellular Models

Cell culture models of toxicity (ref. 79; incorporated by reference in its entirety) use renal tubular cell lines (NRK-52E (refs. 80, 81; incorporated by reference in their entireties), MDCK (ref 17; incorporated by reference in its entirety), RPTEC (ref 82)). Dose response curves are generated at Microbiotix for AuNP-PB*, PB, and AuNP-NC. Orders of magnitude differences between the curves are statistically compared to PB.

Example 3

Measurement of Efficacy of AuNP-PB in a Mouse Model of Pneumonia

Experiments are conducted during development of embodiments herein examine efficacy of AuNP-PB in a mouse model of PA acute pneumonia. Experiments are conducted during development of embodiments herein to identify (i) localized presentation of densely packed arrays of PB on the AuNP surface which increase the bactericidal activity of PB, and (ii) diminished nephrotoxicity may allow higher dosing of AuNP-PB relative to free PB, which may improve efficacy. Experiments are conducted during development of embodiments herein to compare the maximum tolerated dose (MTD) of AuNP-PB* to that of PB.

Figure 17:
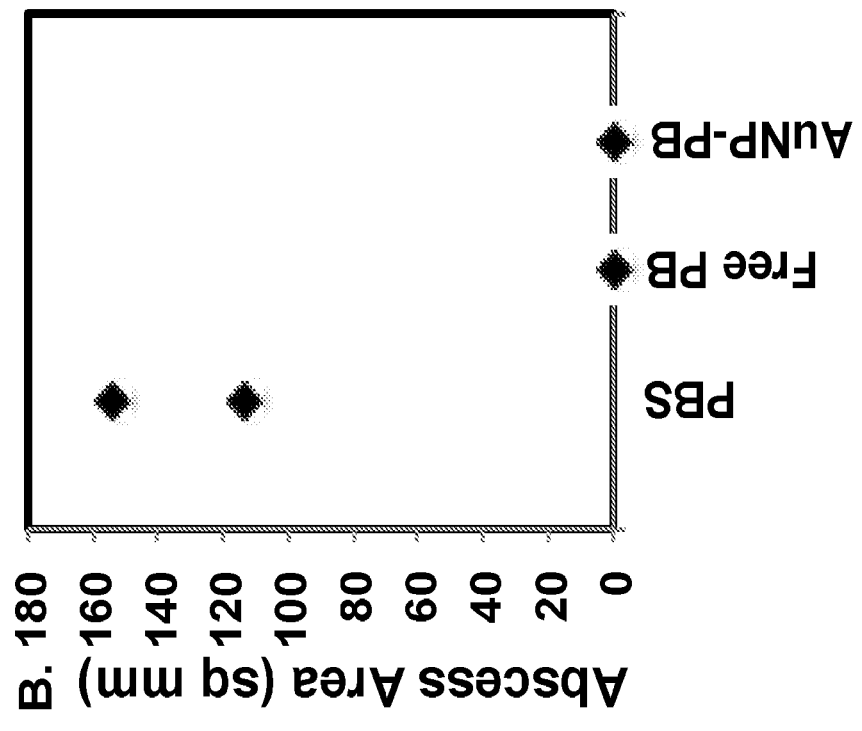
FIG. 17. AuNP-PB administration at time of infection with PA prevents abscess formation. Mice were injected subcutaneously (SC) with $2\times10^6$ CFU of PA strain PA99 in 25 ul of PBS, and were then immediately treated with 50 ul PBS (SC), AuNP-PB (SC, equivalent of 2 ug PB), AuNP (without PB, SC, equivalent amount), or free PB (1 ug IV). SC injections were at the site of the abscess. Abscess areas were measured at 17 hr post-infection. Each symbol represents a distinct mouse. (A) Injections 5 min post-infection; (B) Injections 2 hr post-infection.
Figure 17:
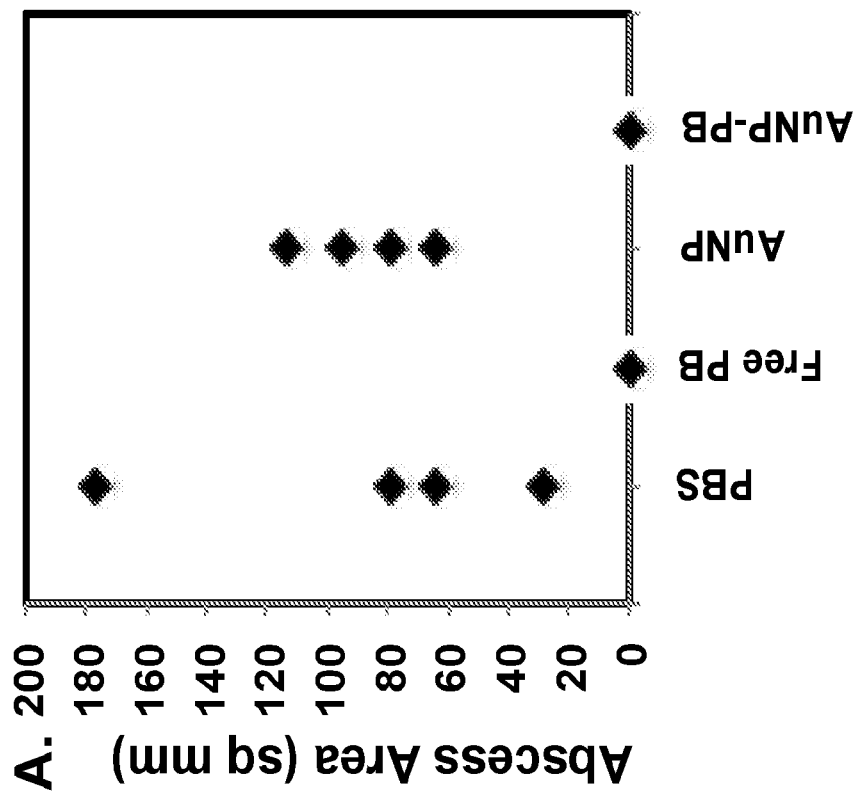

Experiments conducted during development of embodiments herein employed a mouse PA abscess model in which the heterogenous AuNP-PB are injected directly into the site of infection. This assay has the advantage of determining whether AuNP-PB kill bacteria in vivo in the absence of PK concerns. AuNP-PB prevented abscess formation when given at the time of infection or 2 hr after infection (FIG. 17). Bacterial loads were high ($1 \times 10^7$ to $5 \times 10^7$ CFU/abscess) in PBS- or AuNP-NC-treated mice but below the limit of detection for AuNP-PB- and PB-treated mice (data not shown).

The MTD of AuNP-PB* Will be Determined

An appropriate starting dose of free PB in mice is estimated by parameter scaling (ref 57; incorporated by reference in its entirety) to attain $C_{max}$ exposures that approximate concentrations obtained in human serum. A 3 mg/kg PB dose resulted in mean peaks of ~4 mg/L (ref 83; incorporated by reference in its entirety) in mice; hence, 4 mg/kg should result in $C_{max}$ of 5.3 mg/L (or the 50$^{th}$ percentile for human $C_{max}$ after standard dosing) (ref. 84; incorporated by reference in its entirety). Studies are initiated with a PB dose of 4 mg/kg in mice given by tail vein injection every 12 hr. Mice are monitored for 7 days for signs of toxicity (altered respiratory rate, lack of grooming, decreased activity, weight loss). The dose is increased by 1 mg/kg increments until toxicity is observed. Doses that cause more than temporary symptoms are considered the minimal toxic dose, and the next lower dose will be designated the MTD. The MTD of AuNP-PB* is determined in the same manner, starting with the PB molar equivalent MTD of AuNP-PB*.

Test Efficacy of AuNP-PB* in a Mouse Model of PA Acute Pneumonia.

The mouse pneumonia model is used because: (i) ventilator-associated pneumonia (VAP) is a common and severe manifestation of PA and other ESKAPE bacteria (refs. 85-88; incorporated by reference in its entirety); (ii) AuNP-PB achieve relatively high levels in the lungs; and (iii) the mouse model of pneumonia is an accepted and established model for examining the treatment and pathogenesis of PA (refs. 89-91; incorporated by reference in their entireties). Mice are inoculated with $2 \times 10^6$ CFU ($2 \times LD_{50}$) of PA strain PA99 (ref. 92; incorporated by reference in its entirety) by nasal aspiration. Immediately following inoculation, AuNP-PB* or free PB will be given IV by tail vein injection. The MTD of AuNP-PB* is compared for efficacy with the MTD of free PB. Controls will include AuNP-NC (lacking PB) and PBS. In separate experiments, AuNP-PB* is given either 2 hr prior to or 4 hr after inoculation with PA to test prophylactic and therapeutic efficacy, respectively. Mice are euthanized 18 hr after infection and bacterial burden in the lung measured by organ homogenization and plating for CFU enumeration (ref. 39; incorporated by reference in its entirety). CFU values are log-transformed and compared using ANOVA followed by multiple unplanned comparisons with the Tukey-Kramer HSD test with a $\alpha=0.05$. To assess the impact of AuNP-PB* on bacterial dissemination from the lungs to distal organs, the livers and spleens of the same mice are also collected for CFU enumeration. To assess the ability of AuNP-PB* to improve outcomes, separate experiments are performed in which infected ($2 \times LD_{50}$ CFU of PA99) mice are treated (MTD with redosing every 12 hr) and monitored for survival over 7 days. Severely ill mice are euthanized and scored as dead. Kaplan-Meier survival curves will be compared using the log-rank test.

REFERENCES

The following references, some of which are cited above by number, are herein incorporated by reference in their entireties.

1. Presidential Advisory Council. 2015. National action plan for combating antibiotic-resistant bacteria https://www.whitehouse.gov/sites/default/files/docs/national_action_plan_for_combating_antibo tic-resistant_bacteria.pdf. Accessed
2. Boucher H W, Talbot G H, Bradley J S, Edwards J E, Gilbert D, Rice L B, Scheld M, Spellberg B, Bartlett J. 2009. Bad bugs, no drugs: no ESKAPE! An update from the Infectious Diseases Society of America. Clin Infect Dis 48:1-12.
3. CDC. 2013. Antibiotic resistance threats in the United States, 2013. http://www.cdc.gov/drugresistance/threat-report-2013/. Accessed September 18.
4. Payne D J, Gwynn M N, Holmes D J, Pompliano D L. 2007. Drugs for bad bugs: confronting the challenges of antibacterial discovery. Nat Rev Drug Discov 6:29-40.
5. Torrice M. 2013. Antibacterial Boom and Bust. Chem Engineer News 91:34-37.
6. Diseases NIoAaI. 2014. NIAID's Antibacterial Resistance Program: Current Status and Future Directions 2014. https://www.niaid.nih.gov/sites/default/files/arstrategicplan2014.pdf. Accessed
7. Yu Z, Qin W, Lin J, Fang S, Qiu J. 2015. Antibacterial mechanisms of polymyxin and bacterial resistance. Biomed Res Int 2015:679109.
8. Li J, Nation R L, Turnidge J D, Milne R W, Coulthard K, Rayner C R, Paterson D L. 2006. Colistin: the re-emerging antibiotic for multidrug-resistant Gram-negative bacterial infections. Lancet Infect Dis 6:589-601.
9. Dijkmans A C, Wilms E B, Kamerling I M, Birkhoff W, Ortiz-Zacarias N V, van Nieuwkoop C, Verbrugh H A, Touw D J. 2015. Colistin: Revival of an old polymyxin antibiotic. Ther Drug Monit 37:419-427.
10. Bergen P J, Bulman Z P, Saju S, Bulitta J B, Landersdorfer C, Forrest A, Li J, Nation R L, Tsuji B T. 2015. Polymyxin combinations: pharmacokinetics and pharmacodynamics for rationale use. Pharmacotherapy 35:34-42.
11. Garonzik S M, Li J, Thamlikitkul V, Paterson D L, Shoham S, Jacob J, Silveira F P, Forrest A, Nation R L. 2011. Population pharmacokinetics of colistin methanesulfonate and formed colistin in critically ill patients from a multicenter study provide dosing suggestions for various categories of patients. Antimicrob Agents Chemother 55:3284-3294.
12. Rigatto M H, Oliveira M S, Perdigao-Neto L V, Levin A S, Carrilho C M, Tanita M T, Tuon F F, Cardoso D E, Lopes N T, Falci D R, Zavascki A P. 2016. Multicenter prospective cohort study of renal failure in patients treated with colistin versus polymyxin B. Antimicrob Agents Chemother 60:2443-2449.
13. Mammen M, Choi S K, Whitesides G M. 1998. Polyvalent interactions in biological systems: Implications for design and use of multivalent ligands and inhibitors. Angewandte Chemie-International Edition 37:2755-2794.
14. Choi H S, Liu W, Misra P, Tanaka E, Zimmer J P, Itty Ipe B, Bawendi M G, Frangioni J V. 2007. Renal clearance of quantum dots. Nat Biotechnol 25:1165-1170.
15. Alexis F, Pridgen E, Molnar L K, Farokhzad O C. 2008. Factors affecting the clearance and biodistribution of polymeric nanoparticles. Mol Pharm 5:505-515.
16. Tam V H, Schilling A N, Vo G, Kabbara S, Kwa A L, Wiederhold N P, Lewis R E. 2005. Pharmacodynamics of polymyxin B against *Pseudomonas aeruginosa*. Antimicrob Agents Chemother 49:3624-3630.
17. Abdelraouf K, Braggs K H, Yin T, Truong L D, Hu M, Tam V H. 2012. Characterization of polymyxin B-induced nephrotoxicity: implications for dosing regimen design. Antimicrob Agents Chemother 56:4625-4629.
18. Jensen S A, Day E S, Ko C H, Hurley L A, Luciano J P, Kouri F M, Merkel T J, Luthi A J, Patel P C, Cutler J I, Daniel W L, Scott A W, Rotz M W, Meade T J, Giljohann D A, Mirkin C A, Stegh A H. 2013. Spherical nucleic acid nanoparticle conjugates as an RNAi-based therapy for glioblastoma. Sci Transl Med 5:209ra152.
19. Berger T J, Spadaro J A, Chapin S E, Becker R O. 1976. Electrically generated silver ions: quantitative effects on bacterial and mammalian cells. Antimicrob Agents Chemother 9:357-358.
20. Slawson R M, Trevors J T, Lee H. 1992. Silver accumulation and resistance in *Pseudomonas stutzeri*. Arch Microbiol 158:398-404.
21. Zhao G, Stevens S E, Jr. 1998. Multiple parameters for the comprehensive evaluation of the susceptibility of *Escherichia coli* to the silver ion. Biometals 11:27-32.
22. Nirmala G A, Pandian K. 2007. Antibacterial efficacy of aminoglycosidic antibiotics protected gold nanoparticles—a brief study. Colloids Surf A Physiochem Eng Asp 297:63-70.

23. Burygin G L, Khlebtsov B N, Shantrokha A N, Dykman L A, Bogatyrev V A, Khlebtsov N G. 2009. On the enhanced antibacterial activity of antibiotics mixed with gold nanoparticles. Nanoscale Res Lett 4:794-801.
24. Chamundeeswari M, Sobhana S S, Jacob J P, Kumar M G, Devi M P, Sastry T P, Mandal A B. 2010. Preparation, characterization and evaluation of a biopolymeric gold nanocomposite with antimicrobial activity. Biotechnol Appl Biochem 55:29-35.
25. Gu H, Ho P L, Tong E, Wang L, Xu B. 2003. Presenting vancomycin on nanoparticles to enhance antimicrobial activities. Nano Lett 3:1261-1263.
26. Brown A N, Smith K, Samuels T A, Lu J, Obare S O, Scott M E. 2012. Nanoparticles functionalized with ampicillin destroy multiple-antibiotic-resistant isolates of *Pseudomonas aeruginosa* and *Enterobacter aerogenes* and methicillin-resistant *Staphylococcus aureus*. Appl Environ Microbiol 78:2768-27674.
27. Rai A, Prabhune A, Perry C C. 2010. Antibiotic mediated synthesis of gold nanoparticles with potent antimicrobial activity and their application in antimicrobial coatings. J Maer Chem 20:6789-6798.
28. Rashid R, Veleba M, Kline K A. 2016. Focal targeting of the bacterial envelope by antimicrobial peptides. Front Cell Dev Biol 4:55.
29. Eby D M, Farrington K E, Johnson G R. 2008. Synthesis of bioinorganic antimicrobial peptide nanoparticles with potential therapeutic properties. Biomacromolecules 9:2487-2494.
30. Liu L, Xu K, Wang H, Tan P K, Fan W, Venkatraman S S, Li L, Yang Y Y. 2009. Self-assembled cationic peptide nanoparticles as an efficient antimicrobial agent. Nat Nanotechnol 4:457-463.
31. Wang H, Xu K, Liu L, Tan J P, Chen Y, Li Y, Fan W, Wei Z, Sheng J, Yang Y Y, Li L. 2010. The efficacy of self-assembled cationic antimicrobial peptide nanoparticles against *Cryptococcus neoformans* for the treatment of meningitis. Biomaterials 31:2874-2881.
32. Rai A, Pinto S, Velho T R, Ferreira A F, Moita C, Trivedi U, Evangelista M, Comune M, Rumbaugh K P, Simoes P N, Moita L, Ferreira L. 2016. One-step synthesis of high-density peptide-conjugated gold nanoparticles with antimicrobial efficacy in a systemic infection model. Biomaterials 85:99-110.
33. Grace A N, Pandian K. 2007. Antibacterial efficacy of aminoglycosidic antibiotics protected gold nanoparticles—A brief study. Colloids Surf A 297:63-70.
34. Ruden S, Hilpert K, Berditsch M, Wadhwani P, Ulrich A S. 2009. Synergistic interaction between silver nanoparticles and membrane-permeabilizing antimicrobial peptides. Antimicrob Agents Chemother 53:3538-3540.
35. Park S, Chibli H, Wong J, Nadeau J L. 2011. Antimicrobial activity and cellular toxicity of nanoparticle-polymyxin B conjugates. Nanotechnology 22:185101.
36. Nascimento A, Jr., Pontes F J, Lins R D, Soares T A. 2014. Hydration, ionic valence and cross-linking propensities of cations determine the stability of lipopolysaccharide (LPS) membranes. Chem Commun (Camb) 50:231-233.
37. Bagheri M, Beyermann M, Dathe M. 2009. Immobilization reduces the activity of surface-bound cationic antimicrobial peptides with no influence upon the activity spectrum. Antimicrob Agents Chemother 53:1132-1141.
38. Weinstein J, Afonso A, Moss E, Jr., Miller G H. 1998. Selective chemical modifications of polymyxin B. Bioorg Med Chem Lett 8:3391-3396.
39. Shaver C M, Hauser A R. 2004. Relative contributions of *Pseudomonas aeruginosa* ExoU, ExoS, and ExoT to virulence in the lung. Infect Immun 72:6969-6977.
40. Velkov T, Thompson P E, Nation R L, Li J. 2010. Structure—activity relationships of polymyxin antibiotics. J Med Chem 53:1898-1916.
41. Okimura K, Ohki K, Sato Y, Ohnishi K, Uchida Y, Sakura N. 2007. Chemical conversion of natural polymyxin B and colistin to their N-terminal derivatives. Bull Chem Soc Japan 80:543-552.
42. Rocco M, Montini L, Alessandri E, Venditti M, Laderchi A, De Pascale G, Raponi G, Vitale M, Pietropaoli P, Antonelli M. 2013. Risk factors for acute kidney injury in critically ill patients receiving high intravenous doses of colistin methanesulfonate and/or other nephrotoxic antibiotics: a retrospective cohort study. Crit Care 17:R174.
43. Cartin-Ceba R, Kashiouris M, Plataki M, Kor D J, Gajic O, Casey E T. 2012. Risk factors for development of acute kidney injury in critically ill patients: a systematic review and meta-analysis of observational studies. Crit Care Res Pract 2012:691013.
44. Evans M E, Feola D J, Rapp R P. 1999. Polymyxin B sulfate and colistin: old antibiotics for emerging multiresistant gram-negative bacteria. Ann Pharmacother 33:960-967.
45. Jeong E S, Kim G, Moon K S, Kim Y B, Oh J H, Kim H S, Jeong J, Shin J G, Kim D H. 2016. Characterization of urinary metabolites as biomarkers of colistin-induced nephrotoxicity in rats by a liquid chromatography/mass spectrometry-based metabolomics approach. Toxicol Lett 248:52-60.
46. Tarchini G. 2009. Nephrotoxicity associated with intravenous colistin. Clin Infect Dis 49:1773; author reply 1773.
47. Santamaria C, Mykietiuk A, Temporiti E, Stryjewski M E, Herrera F, Bonvehi P. 2009. Nephrotoxicity associated with the use of intravenous colistin. Scand J Infect Dis 41:767-769.
48. Falagas M E, Rizos M, Bliziotis I A, Rellos K, Kasiakou S K, Michalopoulos A. 2005. Toxicity after prolonged (more than four weeks) administration of intravenous colistin. BMC Infect Dis 5:1.
49. Dreaden E C, Austin L A, Mackey M A, El-Sayed M A. 2012. Size matters: gold nanoparticles in targeted cancer drug delivery. Ther Deliv 3:457-478.
50. Anonymous. 1997. Guidance for Industry. M3 Nonclinical Safety Studies for the Conduct of Human Clinical Trials for Pharmaceuticals. U.S. Department of Health and Human Services. Food and Drug Administration. Center for Drug Evaluation and Research (CDER). Center for Biologics Evaluation and Research (CBER).
51. Keirstead N D, Wagoner M P, Bentley P, Blais M, Brown C, Cheatham L, Ciaccio P, Dragan Y, Ferguson D, Fikes J, Galvin M, Gupta A, Hale M, Johnson N, Luo W, McGrath F, Pietras M, Price S, Sathe A G, Sasaki J C, Snow D, Walsky R L, Kern G. 2014. Early prediction of polymyxin-induced nephrotoxicity with next-generation urinary kidney injury biomarkers. Toxicol Sci 137:278-291.
52. Fuchs T C, Hewitt P. 2011. Biomarkers for drug-induced renal damage and nephrotoxicity—an overview for applied toxicology. AAPS J 13:615-631.
53. Simpson D A, Ramphal R, Lory S. 1992. Genetic analysis of *Pseudomonas aeruginosa* adherence: distinct genetic loci control attachment to epithelial cells and mucins. Inf Immun 60:3771-3779.

54. Han W K, Bailly V, Abichandani R, Thadhani R, Bonventre J V. 2002. Kidney Injury Molecule-1 (KIM-1): a novel biomarker for human renal proximal tubule injury. Kidney Int 62:237-244.
55. Sabbisetti V S, Waikar S S, Antoine D J, Smiles A, Wang C, Ravisankar A, Ito K, Sharma S, Ramadesikan S, Lee M, Briskin R, De Jager P L, Ngo T T, Radlinski M, Dear J W, Park K B, Betensky R, Krolewski A S, Bonventre J V. 2014. Blood kidney injury molecule-1 is a biomarker of acute and chronic kidney injury and predicts progression to ESRD in type I diabetes. J Am Soc Nephrol 25:2177-2186.
56. Woods D E, Straus D C, Johanson W G, Berry V K, Bass J A. 1980. Role of pili in adherence of *Pseudomonas aeruginosa* to mammalian buccal epithelial cells. Infect Immun 29:1146-1151.
57. Kenyon E M. 2012. Computational Toxicology. In Reisfeld B, Mayeno A (ed): Volume I, Methods in Molecular Biology, vol 929. Springer Science.
58. Sandri A M, Landersdorfer C B, Jacob J, Boniatti M M, Dalarosa M G, Falci D R, Behle T F, Saitovitch D, Wang J, Forrest A, Nation R L, Zavascki A P, Li J. 2013. Pharmacokinetics of polymyxin B in patients on continuous venovenous haemodialysis. J Antimicrob Chemother 68:674-677.
59. Rhodes N J, Prozialeck W C, Lodise T P, Venkatesan N, O'Donnell J N, Pais G, Cluff C, Lamar P C, Neely M N, Gulati A, Scheetz M H. 2016. Evaluation of vancomycin exposures associated with elevations in novel urinary biomarkers of acute kidney injury in vancomycin-treated rats. Antimicrob Agents Chemother doi:10.1128/aac.00591-16.
60. Sistare F D, Dieterle F, Troth S, Holder D J, Gerhold D, Andrews-Cleavenger D, Baer W, Betton G, Bounous D, Carl K, Collins N, Goering P, Goodsaid F, Gu Y Z, Guilpin V, Harpur E, Hassan A, Jacobson-Kram D, Kasper P, Laurie D, Lima B S, Maciulaitis R, Mattes W, Maurer G, Obert L A, Ozer J, Papaluca-Amati M, Phillips J A, Pinches M, Schipper M J, Thompson K L, Vamvakas S, Vidal J M, Vonderscher J, Walker E, Webb C, Yu Y. 2010. Towards consensus practices to qualify safety biomarkers for use in early drug development. Nature Biotechnology 28:446-454.
61. Leary R, Jelliffe R, Schumitzky A, Van Guilder M. 2001. An adaptive grid nonparametric approach to pharmacokinetic and dynamic (PK/PD) poulation models, p. 389-394. Proceedings of the 14th IEEE Symposium on Computer-Based Medical Systems. CBMS, Bethesda, Md.
62. Tatarinova T, Neely M, Bartroff J, van Guilder M, Yamada W, Bayard D, Jelliffe R, Leary R, Chubatiuk A, Schumitzky A. 2013. Two general methods for population pharmacokinetic modeling: non-parametric adaptive grid and non-parametric Bayesian. J Pharmacokinet Pharmacodyn 40:189-199.
63. Neely M N, van Guilder M G, Yamada W M, Schumitzky A, Jelliffe R W. 2012. Accurate detection of outliers and subpopulations with Pmetrics, a nonparametric and parametric pharmacometric modeling and simulation package for R. Ther Drug Monit 34:467-476.
64. Whited L, Grove M, Rose D, Rhodes N J, Scheetz M H, O'Donnell J N, Neeb J, Thoele K, Jones D R, Lowe C, Moore D, Kiel P J. 2016. Pharmacokinetics of Cefepime in Patients with Cancer and Febrile Neutropenia in the Setting of Hematologic Malignancies or Hematopoeitic Cell Transplantation. Pharmacotherapy doi:10.1002/phar.1807.
65. Rhodes N J, Kuti J L, Nicolau D P, Van Wart S, Nicasio A M, Liu J, Lee B J, Neely M N, Scheetz M H. 2016. Defining Clinical Exposures of Cefepime for Gram-Negative Bloodstream Infections That Are Associated with Improved Survival. Antimicrob Agents Chemother 60:1401-1410.
66. Rhodes N J, Kuti J L, Nicolau D P, Neely M N, Nicasio A M, Scheetz M H. 2016. An exploratory analysis of the ability of a cefepime trough concentration greater than 22 mg/L to predict neurotoxicity. J Infect Chemother 22:78-83.
67. O'Donnell J N, O'Donnell E P, Kumar E J, Lavhale M S, Andurkar S V, Gulati A, Scheetz M H. 2016. Pharmacokinetics of centhaquin citrate in a dog model. J Pharm Pharmacol 68:803-809.
68. O'Donnell J N, Gulati A, Lavhale M S, Sharma S S, Patel A J, Rhodes N J, Scheetz M H. 2016. Pharmacokinetics of centhaquin citrate in a rat model. J Pharm Pharmacol 68:56-62.
69. Rhodes N J, Gardiner B J, Neely M N, Grayson M L, Ellis A G, Lawrentschuk N, Frauman A G, Maxwell K M, Zembower T R, Scheetz M H. 2015. Optimal timing of oral fosfomycin administration for pre-prostate biopsy prophylaxis. J Antimicrob Chemother 70:2068-2073.
70. D'Agostino C, Rhodes N J, Skoglund E, Roberts J A, Scheetz M H. 2015. Microbiologic clearance following transition from standard infusion piperacillin-tazobactam to extended-infusion for persistent Gram-negative bacteremia and possible endocarditis: A case report and review of the literature. J Infect Chemother 21:742-746.
71. Loo A S, Neely M, Anderson E J, Ghossein C, McLaughlin M M, Scheetz M H. 2013. Pharmacodynamic target attainment for various ceftazidime dosing schemes in high-flux hemodialysis. Antimicrob Agents Chemother 57:5854-5859.
72. Patel N, Scheetz M H, Drusano G L, Lodise T P. 2010. Identification of optimal renal dosage adjustments for traditional and extended-infusion piperacillin-tazobactam dosing regimens in hospitalized patients. Antimicrob Agents Chemother 54:460-465.
73. Rhodes N, Kuti J, Nicolau D, Nicasio A, Neely M, Liu J, Lee B, Scheetz M. 2014. Insufficient Cefepime Exposure Predicts Increased Mortality for Gram-negative Bloodstream Infections. Poster Presentation. A-1329, Washington, D C.
74. Rhodes N J, Kuti J L, Nicolau D P, Neely M N, Nicasio A M, Scheetz M H. 2015. An exploratory analysis of the ability of a cefepime trough concentration greater than 22 mg/L to predict neurotoxicity. J Infect Chemother Under review: June 2015.
75. Rhodes N J, MacVane S H, Kuti J L, Scheetz M H. 2014. Impact of loading doses on the time to adequate predicted beta-lactam concentrations in prolonged and continuous infusion dosing schemes. Clin Infect Dis 59:905-907.
76. Reed M D, Stern R C, O'Riordan M A, Blumer J L. 2001. The pharmacokinetics of colistin in patients with cystic fibrosis. J Clin Pharmacol 41:645-654.
77. Wang Y, Jadhav P R, Lala M, Gobburu J V. 2012. Clarification on precision criteria to derive sample size when designing pediatric pharmacokinetic studies. J Clin Pharmacol 52:1601-1606.
78. Vaidya V S, Ozer J S, Dieterle F, Collings F B, Ramirez V, Troth S, Muniappa N, Thudium D, Gerhold D, Holder D J, Bobadilla N A, Marrer E, Perentes E, Cordier A, Vonderscher J, Maurer G, Goering P L, Sistare F D, Bonventre J V. 2010. Kidney injury molecule-1 outperforms traditional biomarkers of kidney injury in preclinical biomarker qualification studies. Nature Biotechnology 28:478-485.
79. Huang J X, Blaskovich M A, Cooper M A. 2014. Cell- and biomarker-based assays for predicting nephrotoxicity. Expert Opin Drug Metab Toxicol 10:1621-1635.
80. Yun B, Azad M A, Nowell C J, Nation R L, Thompson P E, Roberts K D, Velkov T, Li J. 2015. Cellular uptake and localization of polymyxins in renal tubular cells using rationally designed fluorescent probes. Antimicrob Agents Chemother 59:7489-7496.
81. Yousef J M, Chen G, Hill P A, Nation R L, Li J. 2012. Ascorbic acid protects against the nephrotoxicity and apoptosis caused by colistin and affects its pharmacokinetics. J Antimicrob Chemother 67:452-459.
82. Humanes B, Jado J C, Camano S, Lopez-Parra V, Torres A M, Alvarez-Sala L A, Cercenado E, Tej edor A, Lazaro A. 2015. Protective effects of cilastatin against vancomycin-induced nephrotoxicity. Biomed Res Int 2015:704382.
83. He J, Gao S, Hu M, Chow D S, Tam V H. 2013. A validated ultra-performance liquid chromatography-tandem mass spectrometry method for the quantification of polymyxin B in mouse serum and epithelial lining fluid: application to pharmacokinetic studies. J Antimicrob Chemother 68:1104-1110.
84. Sandri A M, Landersdorfer C B, Jacob J, Boniatti M M, Dalarosa M G, Falci D R, Behle T F, Bordinhao R C, Wang J, Forrest A, Nation R L, Li J, Zavascki A P. 2013. Population pharmacokinetics of intravenous polymyxin B in critically ill patients: implications for selection of dosage regimens. Clin Infect Dis 57:524-531.
85. Weiner L M, Webb A K, Limbago B, Dudeck M A, Patel J, Kallen A J, Edwards J R, Sievert D M. 2016. Antimicrobial-resistant pathogens associated with healthcare-associated infections: Summary of data reported to the National Healthcare Safety Network at the Centers for Disease Control and Prevention, 2011-2014. Infect Control Hosp Epidemiol 37:1288-1301.
86. Kalil A C, Metersky M L, Klompas M, Muscedere J, Sweeney D A, Palmer L B, Napolitano L M, O'Grady N P, Bartlett J G, Carratala J, El Solh A A, Ewig S, Fey P D, File T M, Jr., Restrepo M I, Roberts J A, Waterer G W, Cruse P, Knight S L, Brozek J L. 2016. Management of adults with hospital-acquired and ventilator-associated pneumonia: 2016 clinical practice guidelines by the Infectious Diseases Society of America and the American Thoracic Society. Clin Infect Dis 63:e61-e111.
87. Tumbarello M, De Pascale G, Trecarichi E M, Spanu T, Antonicelli F, Maviglia R, Pennisi M A, Bello G, Antonelli M. 2013. Clinical outcomes of Pseudomonas aeruginosa pneumonia in intensive care unit patients. Intensive Care Med 39:682-692.
88. Micek S, Johnson M T, Reichley R, Kollef M H. 2012. An institutional perspective on the impact of recent antibiotic exposure on length of stay and hospital costs for patients with gram-negative sepsis. BMC Infect Dis 12:56.
89. Roy-Burman A, Savel R H, Racine S, Swanson B L, Revadigar N S, Fujimoto J, Sawa T, Frank D W, Wiener-Kronish J P. 2001. Type III protein secretion is associated with death in lower respiratory and systemic Pseudomonas aeruginosa infections. J Infect Dis 183:1767-1774.
90. Cigana C, Bernardini F, Facchini M, Alcala-Franco B, Riva C, De Fino I, Rossi A, Ranucci S, Misson P, Chevalier E, Brodmann M, Schmitt M, Wach A, Dale G E, Obrecht D, Bragonzi A. 2016. Efficacy of the novel antibiotic POL7001 in preclinical models of Pseudomonas aeruginosa pneumonia. Antimicrob Agents Chemother 60:4991-5000.
91. Guo Q, Wei Y, Xia B, Jin Y, Liu C, Pan X, Shi J, Zhu F, Li J, Qian L, Liu X, Cheng Z, Jin S, Lin J, Wu W. 2016. Identification of a small molecule that simultaneously suppresses virulence and antibiotic resistance of Pseudomonas aeruginosa. Sci Rep 6:19141.
92. Shaver C M, Hauser A R. 2006. Interactions between effector proteins of the Pseudomonas aeruginosa type III secretion system do not significantly affect several measures of disease severity in mammals. Microbiology 152:143-152.
93. Feltman H, Schulert G, Khan S, Jain M, Peterson L, Hauser A R. 2001. Prevalence of type III secretion genes in clinical and environmental isolates of Pseudomonas aeruginosa. Microbiology 147:2659-2669.
94. Khlebtsov N, Dykman L. 2011. Biodistribution and toxicity of engineered gold nanoparticles: a review of in vitro and in vivo studies. Chem Soc Rev 40:1647-1671.

The invention claimed is:
1. A composition comprising polymyxin B tethered to the surface of a nanoparticle by a linker, wherein the linker is conjugated to a diaminobutyric acid residue of the polymyxin B.
2. The composition of claim 1, wherein the nanoparticles comprise a gold (Au) or silica core.
3. The composition of claim 1, further comprising additional peptidoglycan-binding antibiotics.
4. The composition of claim 3, wherein the additional peptidoglycan-binding antibiotics are beta-lactams.
5. The composition of claim 1, wherein the linker comprises PEG.
6. The composition of claim 1, wherein the linker comprises an alkyl chain.
7. The composition of claim 1, wherein the linker comprises SH—$(CH_2)_{4-30}(EG)_{2-12}$OH.
8. The composition of claim 1, wherein the linker comprises SH—$C_{11}H_{22}$-$EG_6$OH.
9. A pharmaceutical preparation comprising a composition of claim 1.

* * * * *